(12) United States Patent
Herron et al.

(10) Patent No.: US 6,222,619 B1
(45) Date of Patent: Apr. 24, 2001

(54) DIAGNOSTIC DEVICE AND METHOD

(75) Inventors: James N. Herron; Douglas A. Christensen; Jacob D. Durtschi, all of Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 08/933,203

(22) Filed: Sep. 18, 1997

(51) Int. Cl.$^7$ .......................... G01N 33/48; G01N 21/27; G01J 3/30

(52) U.S. Cl. .......................... 356/39; 356/317; 356/318; 422/82.09

(58) Field of Search .................. 356/39, 317, 318, 356/417; 422/82.06, 82.07, 81, 82.09; 436/66

(56) References Cited

U.S. PATENT DOCUMENTS

| | | |
|---|---|---|
| Re. 33,064 | 9/1989 | Carter et al. ............... 436/34 |
| Re. 34,394 | 9/1993 | Bunting ................... 436/500 |
| 3,748,044 | 7/1973 | Liston . |
| 3,934,061 | 1/1976 | Keck et al. ............... 427/163.2 |
| 3,939,350 | 2/1976 | Kronick et al. ............ 356/36 |
| 4,071,020 * | 1/1978 | Dugliese ................. 422/82.09 |
| 4,166,105 | 8/1979 | Hirschfeld ............... 436/536 |
| 4,264,766 | 4/1981 | Fischer ................... 524/556 |
| 4,298,685 | 11/1981 | Parikh et al. ............. 435/7.5 |
| 4,450,231 | 5/1984 | Ozkan .................... 435/7.92 |
| 4,591,570 | 5/1986 | Chang .................... 435/7.24 |
| 4,818,710 | 4/1989 | Sutherland et al. . |
| 4,857,273 | 8/1989 | Stewart .................. 422/82.11 |
| 4,857,453 | 8/1989 | Ullman et al. ............ 435/7.92 |
| 4,866,681 | 9/1989 | Fertig ..................... 367/140 |
| 4,880,752 | 11/1989 | Keck et al. ............... 435/7.72 |
| 4,892,383 | 1/1990 | Klainer et al. ............ 385/12 |
| 4,893,894 | 1/1990 | Caimi .................... 385/12 |
| 4,909,990 | 3/1990 | Block et al. .............. 422/82.11 |
| 4,913,519 | 4/1990 | Klainer et al. ............ 385/12 |
| 4,940,328 | 7/1990 | Hartman ................. 356/345 |
| 4,945,245 | 7/1990 | Levin .................... 250/461.2 |
| 4,954,318 * | 9/1990 | Yafuso et al. ............. 422/82.09 |
| 5,000,540 | 3/1991 | Nakamura ............... 385/12 |
| 5,006,333 | 4/1991 | Seifer et al. .............. 424/78.05 |
| 5,006,716 | 4/1991 | Hall ....................... 385/12 |
| 5,009,996 | 4/1991 | Shah et al. ............... 435/7.94 |

(List continued on next page.)

FOREIGN PATENT DOCUMENTS

| | | |
|---|---|---|
| 2027434 | 4/1992 | (CA) . |
| 2 220 083 | 12/1989 | (GB) . |
| WO 90/01166 | 2/1990 | (WO) . |
| WO 90/06503 | 6/1990 | (WO) . |
| WO 91/01498 | 2/1991 | (WO) . |
| WO 91/13339 | 9/1991 | (WO) . |

OTHER PUBLICATIONS

Carlsson et al., Protein Thiolation and Reversible Protein–Protein Conjugation, *Biochem. J.*, 173, pp. 723–737, 1978.

Fenton, J.J. et al., "Diagnostic Efficacy of a New Enzyme Immunoassay for Creatine Kinase MB Isoenzyme", 30 *Clin. Chem.*, pp. 1399–1401 (1984).

(List continued on next page.)

*Primary Examiner*—Frank G. Font
*Assistant Examiner*—Amanda Merlino
(74) *Attorney, Agent, or Firm*—Trask Britt

(57) ABSTRACT

A method and apparatus of diagnosing a cardiac disease state in as little as two minutes involving the utilization of an evanescent wave assay system in conjunction with a data acquisition and analysis procedure that monitors the precision of assay results in real time (i.e., while data is being acquired). The method includes diagnosing a disease state using a diagnostic procedure (e.g., an immunoassay) wherein the testing device informs the person conducting the test of the results of the test as soon as reliable test data is obtained (generally, <5% variation in the reaction rate of the assay). After which point, the diagnostic procedure may be terminated.

19 Claims, 16 Drawing Sheets

U.S. PATENT DOCUMENTS

| | | | |
|---|---|---|---|
| 5,043,278 | 8/1991 | Nagaoka et al. | 435/181 |
| 5,059,396 | 10/1991 | Opitz et al. | 422/82.11 |
| 5,064,619 | 11/1991 | Finlan | 422/82.05 |
| 5,081,012 | 1/1992 | Flanagan et al. | 435/7.9 |
| 5,132,095 | 7/1992 | Koshiishi et al. | 422/82.07 |
| 5,156,972 | 10/1992 | Issachar | 422/68.1 |
| 5,156,976 | 10/1992 | Slovacek et al. | 436/64 |
| 5,164,589 | 11/1992 | Sjodin | 250/227.24 |
| 5,166,515 | 11/1992 | Attridge | 250/227.25 |
| 5,173,747 | 12/1992 | Boiarski et al. | 356/361 |
| 5,192,502 | 3/1993 | Attridge et al. | 422/57 |
| 5,192,510 | 3/1993 | Zoha et al. | 422/82.05 |
| 5,202,230 | 4/1993 | Kamentsky | 435/6 |
| 5,212,099 | 5/1993 | Marcus | 436/172 |
| 5,221,958 | 6/1993 | Bohnenkamp | 356/318 |
| 5,224,188 | 6/1993 | Vali | 385/96 |
| 5,248,620 | 9/1993 | Sluka et al. | 436/531 |
| 5,249,251 | 9/1993 | Egalon et al. | 385/123 |
| 5,262,638 | 11/1993 | Egalon et al. | 250/227.14 |
| 5,266,486 | 11/1993 | Fraatz et al. | 435/288.7 |
| 5,268,305 | 12/1993 | Ribi et al. | 436/501 |
| 5,274,721 | 12/1993 | Dickinson et al. | 385/31 |
| 5,290,678 | 3/1994 | Jackowski | 435/7.4 |
| 5,300,423 | 4/1994 | Zoha et al. | 435/7.1 |
| 5,327,225 | 7/1994 | Bender et al. | 356/445 |
| 5,340,715 | 8/1994 | Slovacek et al. | 435/6 |
| 5,340,722 | 8/1994 | Wolfbeis et al. | 435/14 |
| 5,341,805 | 8/1994 | Stavridi et al. | |
| 5,343,550 | 8/1994 | Egalon et al. | 385/13 |
| 5,344,784 | 9/1994 | Attridge | 436/518 |
| 5,354,574 | 10/1994 | Kobayashi et al. | 427/2.13 |
| 5,372,936 | 12/1994 | Fraatz et al. | 435/34 |
| 5,377,008 | 12/1994 | Ridgway et al. | 356/361 |
| 5,399,866 | 3/1995 | Feldman et al. | 250/458.1 |
| 5,401,469 | 3/1995 | Kobayashi et al. | 422/82.07 |
| 5,413,939 | 5/1995 | Gustafson et al. | 436/518 |
| 5,416,579 | 5/1995 | Barshad et al. | 356/300 |
| 5,422,283 | 6/1995 | Ismail | 436/525 |
| 5,426,032 | 6/1995 | Phillips et al. | 435/14 |
| 5,427,915 | 6/1995 | Ribi et al. | 435/7.92 |
| 5,432,096 | 7/1995 | Zhu | 436/171 |
| 5,437,840 | 8/1995 | King et al. | 422/82.08 |
| 5,449,625 | 9/1995 | Kobayashi et al. | 436/518 |
| 5,478,755 | 12/1995 | Attridge et al. | 436/518 |
| 5,492,674 | 2/1996 | Meserol | 422/82.08 |
| 5,494,798 | 2/1996 | Gerdt et al. | 435/6 |
| 5,494,803 | 2/1996 | Carbonell et al. | 435/7.92 |
| 5,514,596 | 5/1996 | King et al. | 436/164 |
| 5,538,850 | 7/1996 | King et al. | 435/6 |
| 5,552,272 | 9/1996 | Bogart | 435/6 |
| 5,580,794 | 12/1996 | Allen | 436/169 |
| 5,604,105 | 2/1997 | Jackowski | 435/7.4 |
| 5,710,008 | 1/1998 | Jackowski | 435/7.4 |
| 5,747,274 | 5/1998 | Jackowski | 435/7.94 |
| 5,814,565 | 9/1998 | Reichert et al. | 422/82.11 |

OTHER PUBLICATIONS

Harrick et al., "Multiple Internal Reflection Fluorescence Spectrometry", *Analytical Chemistry*, vol. 45, No. 4, pp. 687–689, 691, Apr. 1973.

Hirano, K. et al., "Determination of mitochondrial asparatate aminotransferase in serum", 155 *Clin. Chim. ACTA*, pp. 251–262 (1986).

Hoberg, e. et al., Myoglobin, creatine kinase–β isoenzyme, and myosin light chain release4 in patients with unstable angina pectoris, 8 *Eur. Heart J.*, pp. 989–994 (1987).

Ives et al., "Protein Adsorption on the Surface of a Thin–Film Polymer Integrated Optical Waveguide", *Applied Spectroscopy*, vol. 42, No. 1, pp. 68–72, 1988.

Ives et al., "Total Internal Reflection Fluorescence Surface Sensors.", *Optical Fiber Sensors*, pp. 391–396, 1987.

Juronen, E.I. et al., "Rapid, simple and sensitive antigen capture ELISA for the quantitation of myoglobin using monoclonal antibodies", 111 *J. Immunol. Methods*, pp. 109–115 (1988).

Kenett, D., "Quantitative ELISA for human lactate dehydrogenase isoenzyme 5", 9 *J. Immunassay*, pp. 37–49 (1988).

Lee et al., "Protein–resistant surfaces prepared by PEO–containing block copolymer surfactants", *Journal of Biomedical Materials Research*, pp. 351–368 (1989).

Nagai, R. et al., "Clinical application of immunoassays for cardiac myosin light chains", 37 *RINSHO BYORI*, pp. 1353–1359 (1989) (Article in Japanese, English version of abstract also provided).

"OPUS Troponin 1 Calibrators", package insert, 1 page, Aug. 1995.

"OPUS Troponin 1" instructions, 1 page, Feb. 1996.

"OPUS Troponin 1 Controls", package insert, 1 page, Oct. 1996.

Pecht et al., "Kinetics of Antibody–Hapten Interactions", *Molecular Biology, Biochemistry and Biophysics*, pp. 308–309, 311, 313, 315, 317, 319, 321, 323–324, 326, 328, 330, 332, 334, 336, 338, 1977.

Van Steirteghem, A.C. et al., "Comparison of the Effectiveness of Four Clinical Chemical Assays in Classifying Patients with Chest Pain", 28 *Clin. Chem.*, pp. 1319–1324 (1982).

Varasteh, A. et al., "An avidin–biotin ELISA for the measurement of mitochondrial aspartate aminotransferase in human serum", 128 *J. Immunol. Methods*, pp. 203–209 (1990).

Walker et al., "Integrated Optical Waveguide Attenuated Total Reflection Spectrometry and Resonance Raman Spectroscopy of Adsorbed Cytochrome c", *J. Phys. Chem.*, vol. 97, No. 39, pp. 10217–10222, 1993.

Walker et al., "Corning 7059, Silicon Oxynitride, and Silicon Dioxide Thin–Film Integrated Optical Waveguides: In Search of Low Loss, Nonfluorescent, Reusable Glass Waveguides", *Applied Spectroscopy*, vol. 46, No. 9, pp. 1437–1441, 1992.

Werner, M. et al., "Diagnostic Performance of Enzymes in the Discrimination of Myocardial Infarction", 28 *Clin. Chem.*, pp. 1297–1302 (1982).

R. Wurmser, "Thermodynamic study of antigen–antibody reactions", *Experimental Methods in Biophysical Chemistry*, pp. 613–647, no date available.

* cited by examiner

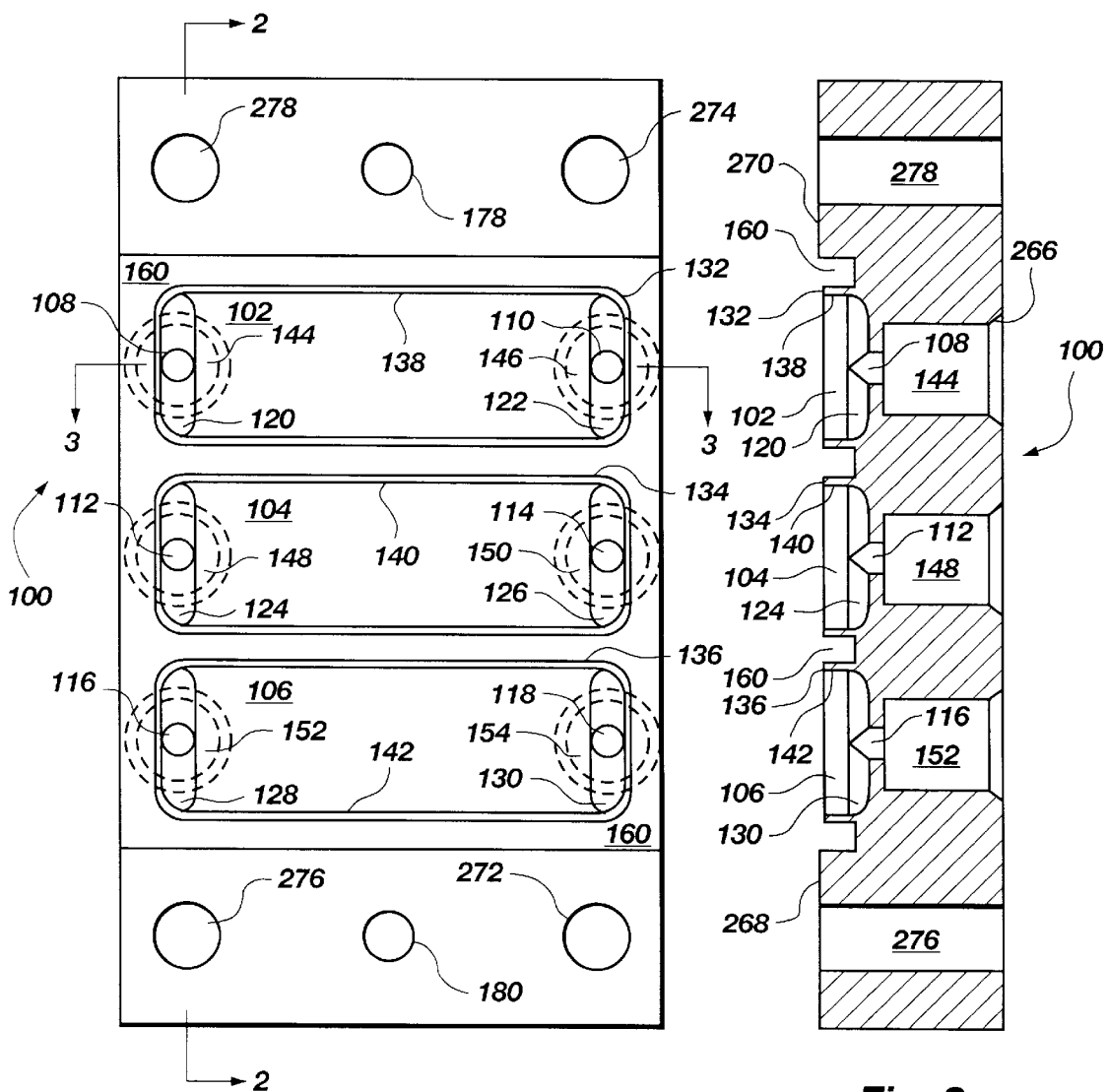
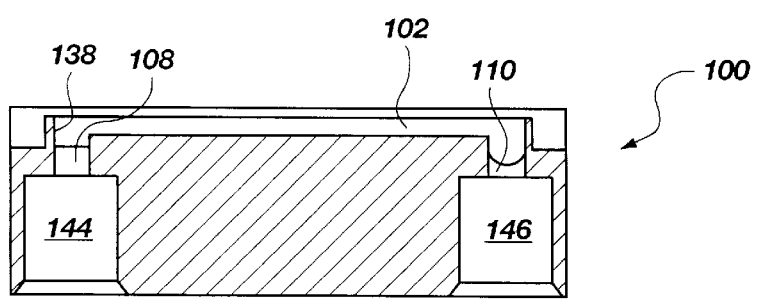
Fig. 1
Fig. 2
Fig. 3

DIAGNOSTIC DEVICE AND METHOD

TECHNICAL FIELD

The invention generally relates to diagnostic devices and, more particularly, to a point-of-care diagnostic device useful in the quick differential diagnosis of a myocardial infarction or similar event in a subject.

BACKGROUND

Various cardiac markers are used in the diagnosis of cardiac function and disease. Among these markers is troponin. Troponin is a protein complex which regulates the contraction of striated muscle. The troponin protein complex includes three distinct proteins. The first is troponin I which is an inhibitory sub-unit. The second is troponin C which is a calcium binding sub-unit. The third is troponin T, a sub-unit which attaches the troponin protein complex to tropomyosin on the thin filament of the striated muscle.

Troponin I is believed to exist in three isoforms, one of which exists in cardiac muscle, while the other two exist in skeletal muscle. The skeletal muscle isoforms are nearly identical, and have molecular weights of about 19,800 Daltons. Structurally, the cardiac isoform of troponin I is about 60% similar to the skeletal isoforms, and has a molecular weight of about 22,500 Daltons.

After the onset of an acute myocardial infarction, the cardiac isoform of troponin I is measurable in the serum after four to six hours. Peak serum concentrations are reached after twelve to eighteen hours after the acute myocardial infarction. Unlike other cardiac markers (e.g., CK-MB and myoglobin), troponin I levels may remain elevated in the serum for several days before returning to normal. Because of these characteristics, the cardiac isoform of troponin I is used in the diagnosis of acute myocardial infarction.

For example, the OPUS Troponin I from Behring Diagnostics, Inc. of Westwood, Mass. is a fluorogenic enzyme-linked immunoassay ("ELISA" or "EIA") for the quantitative measurement of troponin I in serum and heparinized plasma. This assay uses two goat polyclonal antibodies that are purified to recognize different polypeptide segments believed to be unique to the cardiac isoform of troponin I.

As detailed in U.S. Pat. No. 5,604,105, issued Feb. 18, 1997 to Jackowski ("the Jackowski patent"), speed is of the utmost importance in obtaining a reliable diagnosis of an acute myocardial infarction. The choice and efficacy of treatment depends to some extent on obtaining a reliable diagnosis of a myocardial infarction versus some other disease state, such as dyspnea.

In the Jackowski patent, a method and device for diagnosing and distinguishing chest pain is described which reportedly can aid an emergency room physician in determining whether or not a patient is presenting with an ischemic event (e.g., a myocardial infarction or unstable angina). The diagnostic test of the Jackowski patent involves the simultaneous detection of three different cardiac markers in a sandwich assay and provides results to the physician within about one-half hour.

However, time is of the essence with an ischemic event where timely treatment can make the difference between life and death. The present generation of clinical diagnostics assays for cardiac markers, such as CK-MB, myoglobin and Troponin I, typically take on the order of 1 hour to perform. Thus, the time delay of the present generation of clinical diagnostics assays, including the one-half hour delay disclosed in the Jackowski patent, to determine the presence of an ischemic event is unacceptable.

Therefore, it would be a significant improvement in the art if means were available to diagnose such an ischemic event in even a shorter time, e.g., something on the order of two minutes.

DISCLOSURE OF INVENTION

Surprisingly, it has been found that by carefully constructing, selecting, and using a biosensor with a three (or more) cardiac marker system, results can be quickly obtained and reported back to the monitoring physician within, for example, two minutes.

The invention thus includes a method of diagnosing a cardiac disease state in as little as two minutes involving the utilization of an evanescent wave assay system in conjunction with a data acquisition and analysis procedure that monitors the precision of assay results in real time (i.e., while data is being acquired).

For ischemic events, such as an acute myocardial infarction, it has been found that reliable results can be obtained within about 1 to 2 minutes for positive specimens. These results are obtainable because patients suffering from acute myocardial infarctions have elevated levels of the cardiac marker proteins in their blood. For such elevated levels, it takes less reaction time to achieve a given precision in the assay determination.

The invention also includes a method of diagnosing a disease state using a diagnostic procedure (e.g., an immunoassay) wherein the testing device informs the person conducting the test of the results of the test as soon as reliable test data is obtained (generally, <5% variation in the reaction rate of the assay). After which point, the diagnostic procedure may be terminated.

The invention thus also includes diagnostic devices, such as biosensors, which utilize the methods of the invention, and methods of making and using such diagnostic devices.

BRIEF DESCRIPTION OF DRAWINGS

In the drawings, which depict presently preferred embodiments of the invention and in which like reference numerals refer to like parts in different views:

FIG. 1 depicts an enlarged bottom view of the flow cell top which may be used with the invention.

FIG. 2 depicts an enlarged section view of the flow cell top of the preceding figure along section line 2—2.

FIG. 3 depicts an enlarged section view of the flow cell top of FIG. 1 along section line 3—3.

BEST MODE FOR CARRYING OUT THE INVENTION

Figure 4:
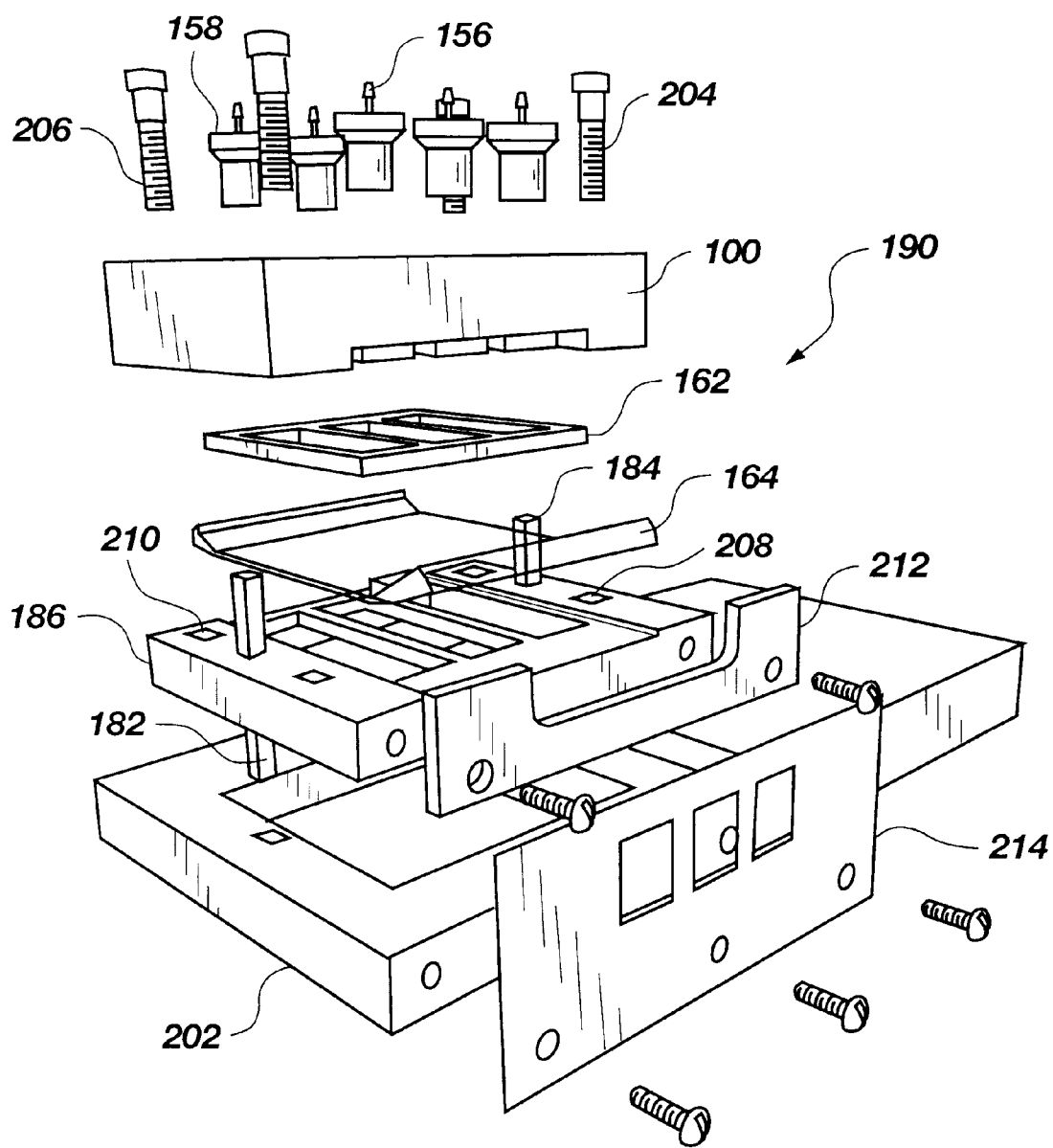
FIG. 4 depicts an enlarged, exploded, perspective view of a biosensor which may be used with the invention.

A. Flow Cell:

The flow cell top, generally 100, depicted in FIGS. 1 through 3, is preferably made of a light absorbing material (e.g., a metal such as aluminum having a passivated surface such as black anodized surface). The depicted flow cell top 100 is generally plate-like, and is formed to contain a plurality of wells or reservoirs 102, 104, 106 (for example, two to ten reservoirs).

A design with at least two individual reservoirs has significant advantages over a single reservoir embodiment, for instance when it is desirable to measure the test sample fluorescence simultaneously with fluorescence from a "control" region on the same waveguide. For example, the level of non-specific binding to the waveguide (or non-specific fluorescence) can be subtracted from the test sample fluorescence. Also, measurement changes due to fluctuations in intensity of the exciting light can be corrected. In a displacement assay, the "control" region could be a pre-loaded waveguide with no analyte present in the sample, or with a known amount of analyte. With the depicted embodiment of three or more wells, fluorescence can be measured for both a no-analyte control and at least one known calibration analyte sample in addition to the "unknown" or test sample. However, even with a single reservoir, the invention is able to analyze multiple analytes in a single sample (e.g., by use of a single waveguide in multiple experiments).

In the depicted embodiment, the reservoirs 102–106 have respective inlet/outlet apertures 108, 110, 112, 114, 116, 118 extending through the flow cell top 100 for injecting and withdrawing the liquid to be analyzed into the reservoirs 102–106. In some cases, this liquid may be oscillated into and out of the reservoir with a pump, which enhances the mixing of the analyte and reactant. With oscillation, the performance (e.g., speed) of the assay is increased. In the depicted embodiment, each aperture 108–118 is associated with its own depressed recess 120, 122, 124, 126, 128, 130 formed in the flow cell top 100.

Between the recesses associated with a particular reservoir, lateral or longitudinal channels may be formed in the flow cell top to aid in mixing the liquid contained within the reservoir (not shown).

In the depicted embodiment, the outer periphery of the reservoirs 102–106 are each defined by respective walls 132, 134, 136 which are preferably integrally formed with the rest of the flow cell top 100, although they may be a separate component of the flow cell top. The inner circumferences 138, 140, 142 of the walls 132–136 are made of an inert, opaque material such as an inert, opaque plastic, or a metal such as passivated, black anodized aluminum, copper, stainless steel, or similar alloy. In the depicted embodiment, the entire flow cell top 100 is made of a metal, while in other embodiments (not shown), the flow cell top may be made of a non-metallic material, and an opaque, dark material or metal sleeve placed within the reservoirs (not shown). Material in contact with the liquid should exhibit low protein absorption properties.

Accordingly, a metal, a hydrophilic non-metallic material or a hydrophobic nonmetallic material coated with a thin film of hydrophilic material (e.g., PEG, PLURONICS or other hydrogels) may be used.

In the depicted embodiment, the apertures 108–118 associated with the respective reservoirs 102–106 fluidically communicate the recessed portions 120–130 of the reservoirs with a pair of respective receptacles 144, 146, 148, 150, 152, 154 (shown by construction lines in FIG. 1) for receiving fluid inlet/outlet ports 156, 158 which are associated with the flow cell top 100 (FIG. 4). Although the fluid inlet/outlet ports 156, 158 will be described with regard only to one reservoir, it is to be understood that the description applies likewise for the other reservoirs of the flow cell top (if any).

As depicted in FIG. 4, the fluid inlet/outlet ports 156, 158 may be male threaded nipples which interact with corresponding threaded members (threads not shown) bored into the flow cell top 100. The open ends of the nipples are in fluid communication (e.g., by tubing or other conduit—FIG. 8) with, for example, a syringe pump (not shown). Other fluid tight arrangements between the ports and the flow cell top can be used, so long as the sample fluid communicates with the apertures 108–118. The liquid to be analyzed (e.g., whole blood, plasma, diluents, or mixtures thereof) can thus be injected and withdrawn from the reservoirs 102–106 by use of, for example, an oscillating pump (not shown).

As further depicted in FIGS. 1 and 4, the outer peripheries of the walls 132-136 also partially define a recess 160 formed in the flow cell top. This recess 160 is formed to accept a gasket 162 (FIGS. 4 & 5) which is more thoroughly described hereinafter. This gasket 162 cushions placement of a waveguide onto the flow cell top 100 and impedes slippage of the waveguide when associated with the flow cell top. As is also more thoroughly described herein, the gasket, preferably, does not serve as any part of the walls 132–136 to contain the liquid within a reservoir 102–106. The flow cell may be used with a quartz waveguide or, more preferably, with the hereinafter described plastic molded waveguide 164.

Figure 6:
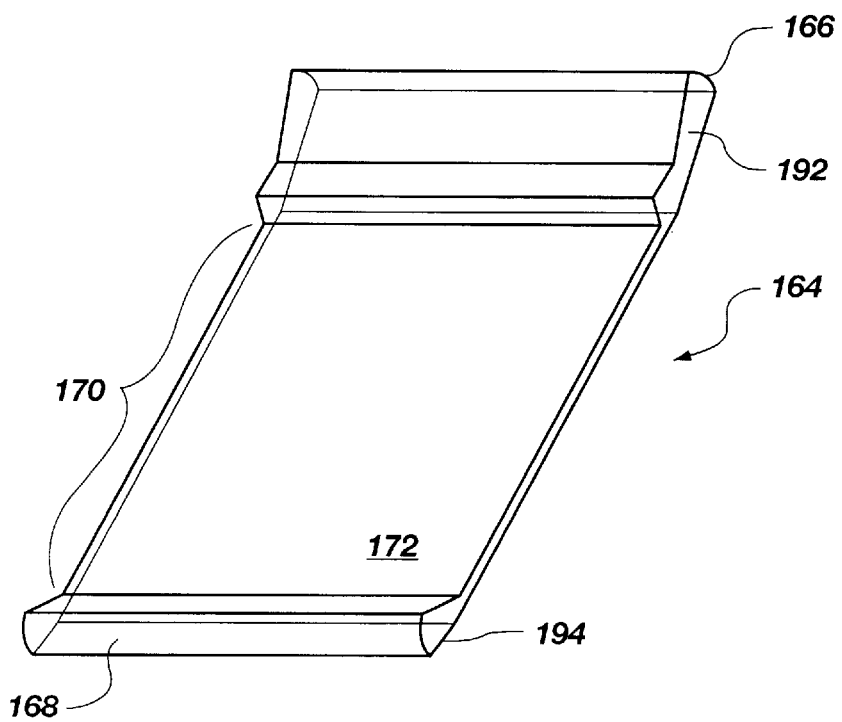
FIG. 6 depicts an enlarged view of a plastic, molded flat waveguide with integrated input and output coupling lenses.
Figure 7:
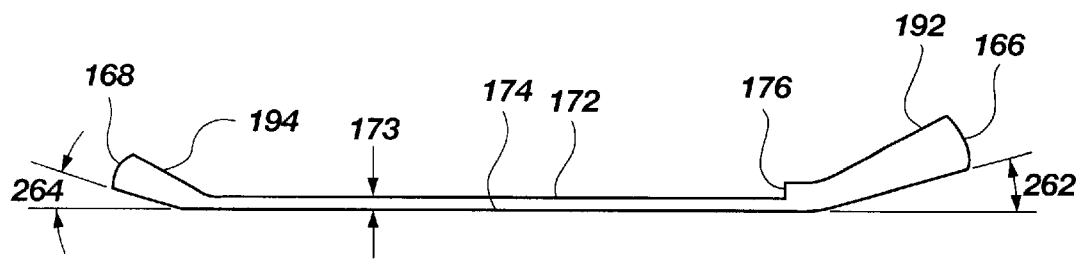
FIG. 7 is an enlarged side view of the waveguide of the preceding figure.
Figure 9:
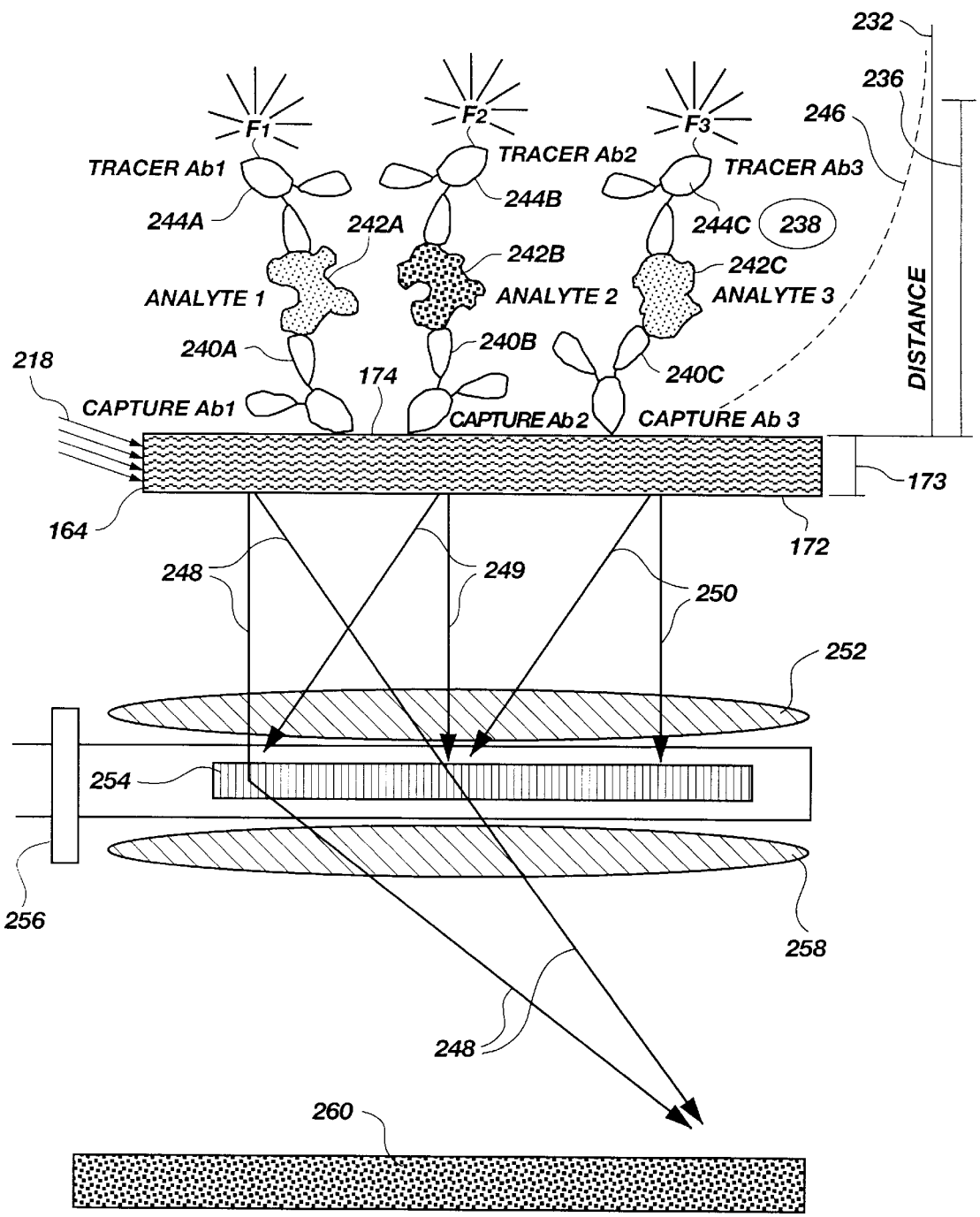
FIG. 9 is a stylized, enlarged side view of a portion of a waveguide and biochemical components of a immunofluorescent assay for use with the invention illustrating spatially-resolved detection of fluorescence emitted from a planar waveguide sensor using different capture molecules and tracer molecules for detecting different analytes of interest in a sample solution.

B. The Waveguide:

As depicted in FIGS. 4, 6 & 7, a preferred waveguide 164 is a plastic molded waveguide (e.g., molded of an optical plastic, such as polystyrene) having integrated input 166 and output 168 coupling lenses. Such a waveguide 164 is preferably sled-shaped, having a planar (optical substrate) portion 170 with first 172 and second 174 parallel plane surfaces and an edge having a thickness 173 therebetween (FIGS. 6 and 7). At least one of the waveguide surfaces 172 has a plurality of the selected capture molecules 240A, 240B, and 240C associated therewith (e.g., immobilized thereon as depicted in FIG. 9), although other methods of bringing the capture molecules into sufficiently close association with the surface may be used (e.g., by placing a strip immunoassay onto the waveguide surface, or using a fibrous "mat" with capture molecules attached to the fibers). These surfaces 172, 174 should have the best optical smoothness possible. The thickness will typically be between 0.20 and 1.0 millimeter ("mm"), more preferably about 0.5 mm.

The edge of the planar portion has a receiving region (e.g., lens 166) for receiving light to be internally propagated. In the embodiment depicted in FIGS. 6 & 7, an input or receiving lens 166 is integrally adapted to the waveguide adjacent the receiving region at the "front" of the waveguide. Other methods of optically associating the lens to the planar portion could also be used. Surface specifications for such a lens or lenses are similar to the planar or "plate" portion of the waveguide. A maximum roughness amplitude of 0.013 to 0.025 $\mu$m (0.5 to 1 $\mu$in) is preferred. Preferably, machine lines should be parallel (vertical when looling at lens) to the long axis of the waveguide. Surface specifications for the side of the part and lens ramp areas are less stringent than the top and bottom surfaces of the plate structure.

In another embodiment (not shown), the lens (or lenses) is not integrally associated with the waveguide, but is adapted to interact optically with the waveguide, or multiple waveguides.

Alternatively, rather than using a lens to couple light into the waveguide, a grating could be used. Various gratings as well as methods for incorporating them into a waveguide are known. See, e.g., U.S. Pat. No. 5,480,687, issued Jan. 2, 1996 to Heming et al., at column 4, lines 1–10, and column 6, line 20 to column 7, line 55, U.S. Pat. No. 5,081,012, issued Jan. 14, 1992 to Flanagan et al., U.S. Pat. No. 5,455,178, issued Oct. 3, 1995 to Fattinger, U.S. Pat. No. 5,442,169, issued Aug. 15, 1995 to Kunz, and U.S. Pat. 5,082,629, issued Jan. 21, 1992 to Burgess, Jr. et al. Gratings may be fabricated by a number of means including but not limited to: embossing, molding, photolithography, direct etch electron beam lithography, interference lithography, and phase shift lithography. Embossed gratings are mechanically stamped or thermally imbued onto a surface and thereupon affixed to a substrate. Photolithographic gratings are formed from the chemical development and etching of photoresist and substrate after masked illumination by an appropriate source. Interference and phase shift lithography are similar techniques which allow finer resolution of etched structures than does conventional photolithography. Ion or particle beam methods fabricate precise gratings by directly etching or "writing" a grating substrate with a stream of ions or molecular particles.

The grating itself can consist of an etched pattern of regular features in a metal film coated onto the planar portion of the waveguide or the front ramp. Standard diffraction gratings such as those used in spectrometers like "replica" gratings (gratings comprised of a dried epoxy coated with metal) can be used. The use of such grating couplers helps to avoid fabrication complexities associated with the use of a receiving lens or plasma-etched gratings. The procedure for applying such couplers is presently used to emboss holograms onto plastic credit cards, and, using such a process, the coupler could be mass produced at a relatively low cost.

Figure 12:
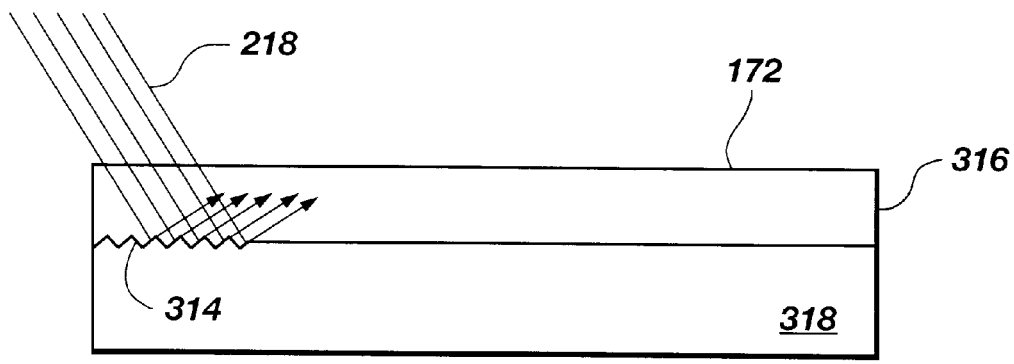
FIG. 12 depicts an enlarged, stylized, side view of a portion of a plastic film waveguide having an optical diffraction grating coupler.
Figure 13:
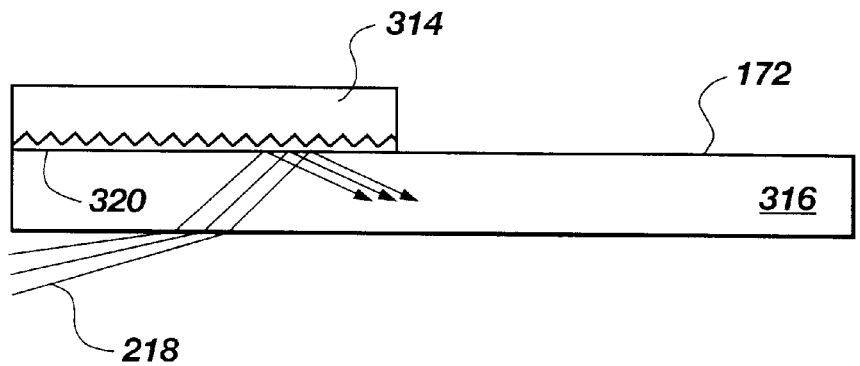
FIG. 13 depicts an enlarged, stylized, side view of a portion of a plastic film waveguide to which a separate optical diffraction grating has been associated.

In an alternative embodiment shown in FIG. 12, a corrugated waveguide with gratings 314 (>5 nm deep or thick) is associated with (e.g., molded on, adhered to, or hot stamped onto or embossed onto) the receiving region of a plastic thin film waveguide 316 (or a cast thin plastic planar waveguide) associated with (e.g., adhered to) a lower index substrate 318. Although in the depicted embodiment, the grating 314 is positioned between the thin film and the lower index substrate, other orientations such as applying the grating to the surface 172 of the thin film waveguide could also be used (not shown). Also, alternatively, the light could be directed into the waveguide from a different direction. In any event, the grating receives light 218 to be internally propagated within the waveguide 316. In such a case, the waveguide portion 316 will typically be made of a transparent optical plastic and have a thickness of from about 10 micrometers to about 200 micrometers, preferably about 125 micrometers. In the case of extremely thin waveguide films (e.g., about 10 to 25 $\mu$m), the resulting film may be attached to a preferably rigid, open support structure. Alternately, the resulting thin film may be affixed to a supporting substrate having a lower index of refraction than the film (FIG. 12).

From efficiency measurements, it can be determined that for an integrated optic waveguide-fluoroimmunoassay, the most efficient etch depths are about 1.5 times that of the grating period. For diffraction to occur in a grating, the period "d" should be on the order of the wavelength of light (lambda). Given the path length difference, $\delta$, between the light rays from two neighboring grating features (slits, rigids, and the like), a constructive interference pattern is established by the light leaving the grating when $\delta$ is an integer multiple, m, of the wavelength.

$$\delta = d(n_t \sin \Theta_t - n_i \sin \Theta_i) = \text{lambda}(m)$$

wherein d is the grating period, $\Theta_t$ and $\Theta_i$ are the transmitted and incident angles at the grating interface (measured relative to the surface normal), and $n_t$ and $n_i$ are the refractive indices of the transmitting and incident mediums (i.e., the waveguide and the substrate). Using this formula, one determines that the incident angle for coupling 632.8 nm light is 38.03° when the grating period is 0.7 $\mu$m.

The angle of incidence of light from air into the lowest order made of the waveguide and the groove density into waveguide films can be calculated by the use of the equation above, and was determined to be 4.6°, 27.4° and 57.2° for polystyrenes having densities of 2400 g/mm, 1800 g/mm, and 1200 g/mm, respectively, for incident light of 632.8 $\mu$m wavelength.

In still other embodiments, laser light may be prism-coupled onto an integrated optic waveguide ("IOW") (not shown), end-fire coupled (i.e., direct focusing of light into the waveguide), or taper-coupled (e.g., by use of an adlayer film tapered in thickness or refractive index, preferably in conjunction with a grating coupler) into the waveguide (also not shown).

In order to taper-couple light into the flow cell, a gentle tapered section (e.g., either curved or linear) can be used to "funnel" light into the end of a thin planar waveguide. A well-colimated input beam (e.g., a laser) couples into a multi-mode waveguide (e.g., about 50 μm in thickness) due to the "Law of Brightness" constraint (i.e., the product of the beam extent and numerical aperture is a constant through the taper). The taper may be also coupled with a lens.

The waveguide depicted in FIGS. 6 & 7 has a shelf or ridge 176. The ridge 176 abuts against an edge of the flow cell top when the waveguide 164 is functionally associated with the flow cell top (FIG. 4). As shown (FIG. 1), the flow cell top 100 has two apertures 178, 180 which interact with registration members ("registration pins") 182, 184 of a second frame member ("flow cell bottom") 186 structured to interact with the flow cell top 100 and waveguide 164 in order to hold ("sandwich") the waveguide in place (FIG. 4).

Figure 8:
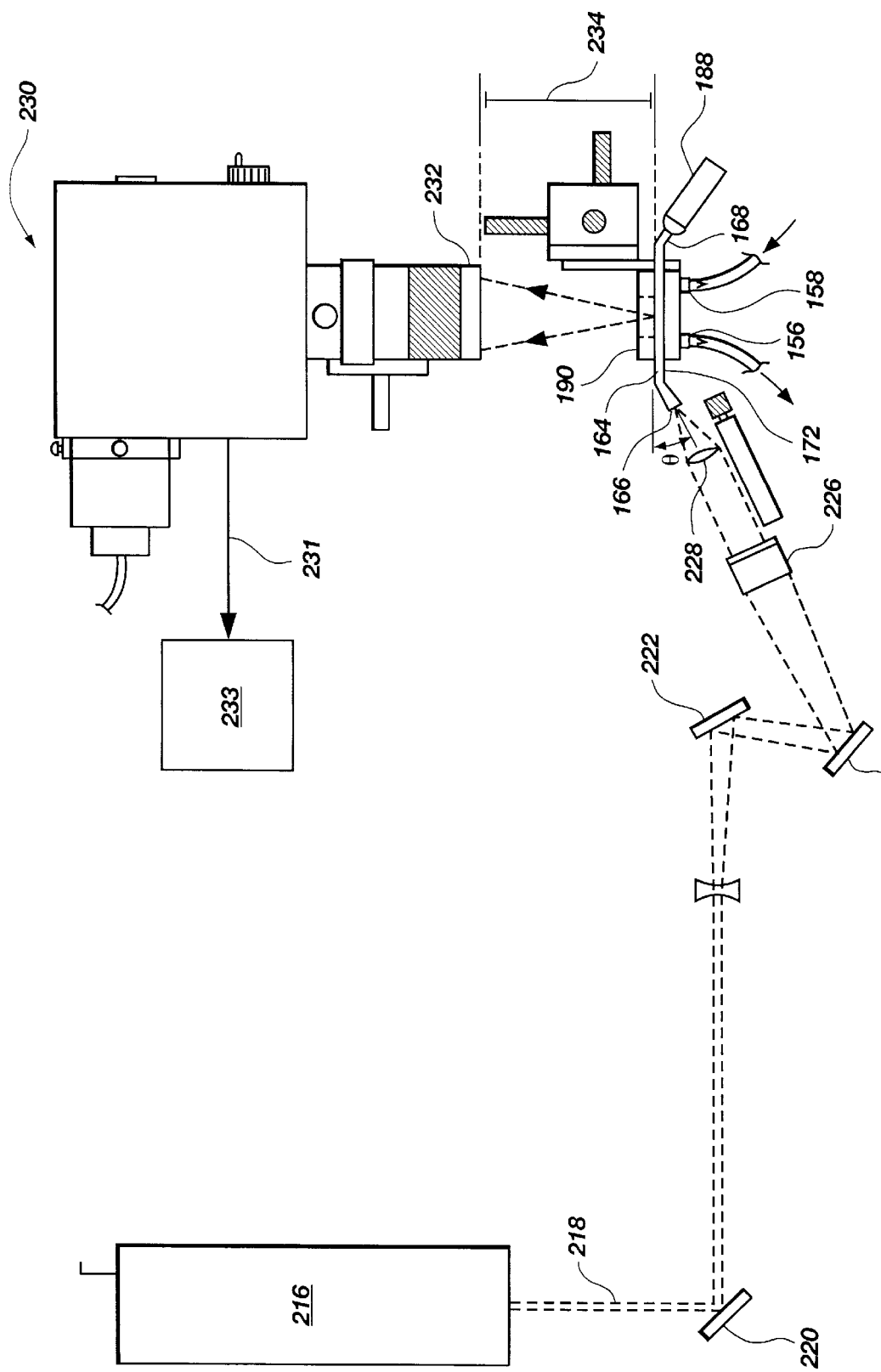
FIG. 8 is a schematic diagram of a fluorescent assay apparatus useful for practicing the invention, showing the flow cell assembly of FIG. 4 in a particularly useful orientation with respect to the earth.

Laser light preferably enters the receiving lens 166 at mean angle $\Theta$ (FIG. 8). The mean angle $\Theta$ will typically vary dependent upon the type of material used to form the waveguide and the optical properties of the media opposite both faces of the waveguide. When the waveguide or waveguide layer is made of polystyrene (e.g., NOVOCOR™), then the mean angle will generally be less than 32°, e.g., 15° to 25°. Typical beam widths vary from 0.5 to 2.0 mm.

On the other side of the waveguide, an outcoupling 188 interacts with the rear or output lens 168 to ensure that light is detected (FIG. 8). The outcoupling 188 may be a single photodetector, multiple photodetectors, (a preferably cooled, e.g., −22° C.) standard CCD (charge-coupled device) or like device. The light passing through the waveguide 164 and received by the outcoupling 188 is analyzed for quality and/or intensity. Unlike the end collection of light described in U.S. Pat. No. 4,582,809, issued Apr. 15, 1986 to Block et al., in the present invention, the light may be detected at the end of the waveguide for two reasons. The first reason is as a quality control measure. The light passing through the waveguide may be measured so that the operator of the device knows that the biosensor has been properly placed in the apparatus and that the light source is still working. Alternatively, the device may be configured so that a predetermined strength of light must first be detected at the rear lens 168 before the apparatus will operate, again to ensure that the flow cell assembly ("biosensor"), generally 190, has been properly placed. The second reason is that end detection involves calibration of the device to ensure that the amount of light traveling through the waveguide is uniform, and, if it is not uniform to accommodate any differences. The light outcoupled from the lens 168 associated with the rear of the waveguide is preferably measured over the width of the lens to ensure that sufficient light is passing through the lens to create detectable fluorescence.

Preferably, a plastic waveguide such as that depicted in FIGS. 6 & 7 will be made (e.g., injection-molded) of an optical plastic such as polystyrene, polymethylmethacrylate ("PMMA"), polycarbonate or equivalent material, and will have a refractive index greater than 1.33 (the index of water being 1.33). The size of the waveguide will depend on its desired use.

Although the front lens ramp 192 and rear lens ramp 194 are shown in a "concave" or arced position relative to one another and the planar portion 170 (FIG. 7), the ramps need not angle towards a common center, and one of the lens ramps could be angled in the opposite direction from the plane of the planar portion, and the ramps would fall in roughly parallel planes (not shown).

In another embodiment (not shown), the waveguide includes a laminate of layers, one layer serving as a structural substrate, and the other (e.g., thin film SiON) serving to transmit the light, such as those disclosed in International Application No. PCT/US96/02662 (International Publication No. WO 96/26432, published Aug. 29, 1996) to the University of Utah Research Foundation. In such an embodiment, the structural substrate can be made of a plastic such as polystyrene, PMMA, polyvinyl chloride ("PVC"), polyimide, polyester, polyurethane, organically modified ceramics, polymers of diethylene glycol bisallyl carbonate, allyldiglycolcarbonate, polycarbonate, or equivalent material. The waveguide layer is preferably an optical plastic such as polystyrene, although it can be made of other suitable materials such as $TiO_2$, a mixture of $TiO_2$—$SiO_2$, $SiO_2$, $ZnO$, $Nb_2O_5$, $Si_3N_4$, $Ta_2O_5$, $HfO_2$, or $ZrO_2$. Waveguide layers such as $TiO_2$, $SiO_2$, or $Si_3N_4$ can be deposited by plasma chemical vapor deposition ("PVCD"), plasma impulse chemical vapor deposition ("PICVD") process, or the like.

Figure 5:
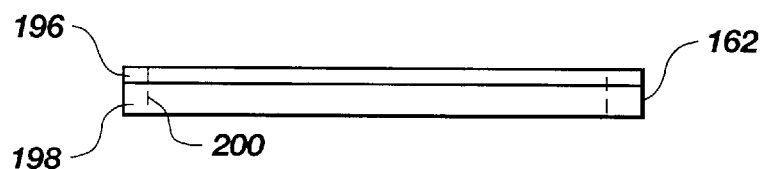
FIG. 5 depicts an enlarged, side view of a laminated gasket which interacts with the flow cell top of FIG. 1.

C. Gasket:

A gasket 162 is preferably seated between waveguide 164 and flow cell top 100 (FIGS. 4 & 5). A preferred gasket 162 for use with the waveguide 164 with integrated lenses includes a clear TEFLON® layer 196 adhered (e.g., with the use of a suitable glue or double-sided tape, such as MAC-TAC No. SB 1154 available from Morgan Adhesives Co. of Stow, Ohio, USA) to a silicon rubber gasket 198 shaped to fit the recess of the flow cell top. Alternatively, synthetic resin polymers (i.e., TEFLON®-like materials) may be used. The depicted gasket 162 is configured with three internal openings (construction lines 200 of FIG. 5) which surround but do not interact with the reservoirs 102–106.

Upon assembly of the biosensor in the reservoirs 102–106, the first planar surface 172 of the waveguide 164 constitutes a floor or ceiling (FIG. 8) of the particular reservoir, while the flow cell top 100 is formed to constitute the ceiling or floor and the walls. The orientation depicted in FIG. 8, wherein the planar surface 172 serves as a ceiling and lays level with the earth has been found to be especially useful, enhancing the ability of the device to detect the presence of target molecules in whole blood over a shorter period of time (e.g., five to ten minutes), especially with oscillation. However, it is, of course, understood that the flow cell assembly 190 may be oriented in any position (e.g., vertical or any angle). Angling the flow cell assembly 190 assists in removing bubbles or heavy materials away from the waveguide 164, if desired. Alternatively, a dye can be incorporated into the sample solution for absorbing interfering signals. Although the reservoirs 102–106 are here shown to be generally rectangular in shape, other shapes could be used.

The gasket 162 is preferably made of a semi-rigid material having an index of refraction less than that of the waveguide material in the wavelength range of the exciting light. For best results, it is believed that the index of refraction of the gasket material should be as low as possible compared to that of the waveguide. For a waveguide made of quartz or glass, the index of refraction would typically be from about 1.46 to 1.52, higher for high-lead glass. A transparent (non-pigmented) silicon rubber (siloxane polymer) with an index of refraction of 1.35–1.43 is a presently preferred material for gasket 162. TEFLON® or TEFLON®-type materials such as PTFE (polytetrafluoroethylene) or FEP (fluorinated ethylene propylene) have indices of refraction of around 1.34–1.35, and may also be suitable for use as layer 196.

The other portion 198 of the gasket may be formed of an opaque (e.g., red or black) neoprene or silicon rubber material which is preferably biologically inert although due to the metal walls, it need not be.

D. The Flow Cell Assembly

Figure 11:
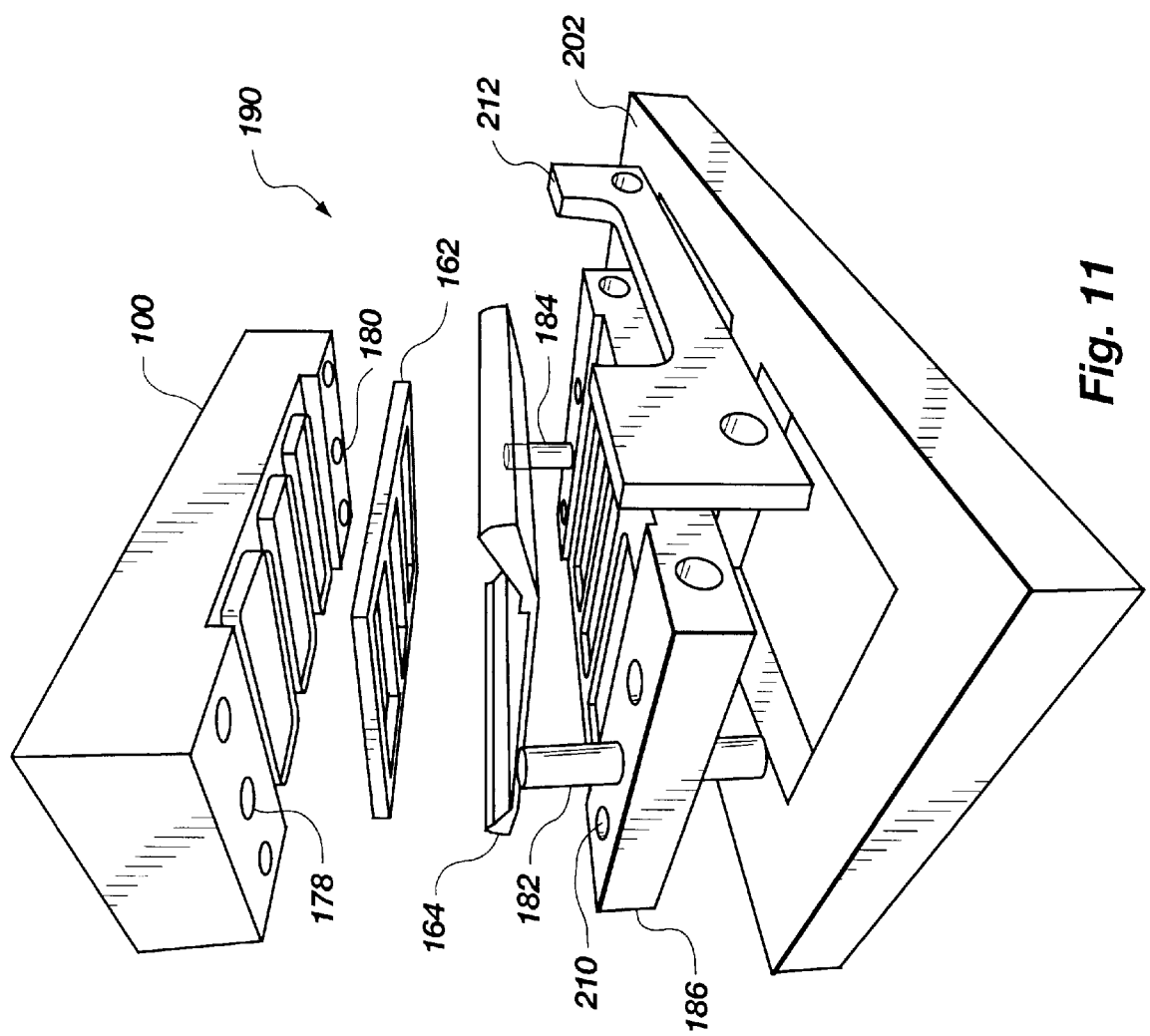
FIG. 11 depicts an enlarged, exploded, perspective view of a biosensor according to the invention.

As depicted in FIG. 11, a preferred flow cell assembly biosensor 190, according to the invention, generally includes a flow cell portion, gasket 162, and waveguide 164. The flow cell portion includes the flow cell top 100, flow cell bottom 186, and a flow cell stage (or "flow cell platform") 202. As shown in FIG. 8 and, as more thoroughly described herein, these three components of the biosensor 190 are integrated with one another in such a manner that excitation light enters the front lens 166 of the waveguide 164, travels through the front lens ramp 192 and planar portion 170, and passes out of the rear lens ramp 194 and rear lens 168 to the outcoupling 188.

The flow cell assembly can also include means for associating the flow cell top 100 with the flow cell bottom 186, thus sandwiching the gasket 162 and waveguide 164 therebetween. The depicted means for doing so are threaded clamping bolts 204, 206 which interact with correspondingly threaded holes 208, 210 in the flow cell bottom 186. Of course, however, equivalent means such as screws, nuts and bolts, clamps, snap fits, and the like, could alternatively be used.

A waveguide registration plate 212 is shown associated with the flow cell bottom 186 (FIG. 4). The waveguide is reproducibly positioned between the flow cell top and bottom when aligned with the registration plate 212. Also depicted is a 3-channel beam mask 214 having three apertures for receiving a light beam.

E. The Apparatus:

Once the flow cell top 100, gasket 162 and particular waveguide 164 have been associated with one another, the thus formed biosensor 190 may be used in an apparatus for performing immunoassays such as fluoroimmunoassays. As depicted in FIG. 8, such an apparatus includes a light source 216 which provides a light beam 218 which is directed by means of mirrors 220, 222, 224 to an optical biosensor 190. The light source 216 may be an argon laser or laser diode capable of emitting at center wavelengths of between 488 and 514.5 nm and 600 to about 900 nm (e.g., 633 nm), respectively.

The embodiment of FIG. 8 further includes a 45° angle mirror 226 which is positioned for assisting in focusing the beam 218 onto the input lens 166 of a particular biosensor 190, if desired. In the case of a non-integrated quartz waveguide, a focusing lens 228 is preferably positioned between angle mirror 226 and the biosensor 190, for focusing light from beam 218 onto the end of the biosensor. Focusing lens 228 is removable, and is depicted mounted on an X-Y translation unit so that its position may be adjusted for best focusing. Furthermore, the translation unit can be moved to adjust the angle Θ for waveguides of differing composition. A significant portion (in the case of the quartz waveguide, the entire portion) of the optical substrate 164 is of a generally planar shape having two planar surfaces spaced by a width 173, as shown in FIG. 9, which is more thoroughly described herein.

Light detection means, generally 230, are positioned to detect and/or measure fluorescent light emitted from the biosensor 190. As more thoroughly described herein with regard to FIG. 9, the emitted light is reflective of the concentration of a selected analyte in a sample. The light detection means 230, depicted in FIG. 8, includes a collection lens 232 positioned to collect the emitted fluorescence from a direction substantially orthogonal to the direction of propagation of light beam 218 through waveguide 164.

The distance 234 between collection lens 232 and waveguide 164 is selected, as known to those skilled, to maximize the collection of light emitted from the region of evanescent light penetration while at the same time imaging this light onto the face of the photodetector. The light collected by collection lens 232 is then sent to detection means 230, which responds by outputting signals 231 reflective of the level of collected fluorescent light. The output signals 231 are transmitted to a controller 233, including monitoring means, which monitors the intensity of the output signals 231 over time and determines presence or absence of the selected analyte in the sample.

Detection means 230 may be any type of photodetector useful to detect light in the wavelength region spanning the wavelength range of the emitted fluorescence, as known in the art. However, in a preferred embodiment for simultaneous multi-analyte assays, detection means 230 is an imaging-type detector providing direct imaging of each of the fluorescent signal(s) originating in the evanescent zone 236 (FIG. 9). In the apparatus of FIG. 8, detection means 230 is a CCD detector which produces a signal. Such imaging signal collection provides simultaneous measurement of multiple samples in a much simpler way than a system in which a separate optical element is needed to read each well or patch. The present imaging detection system also provides for collection of emitted fluorescence directly from the evanescent zone 236, rather than via evanescent penetration of the fluorescence into the waveguide (FIG. 9).

Alternatively, detection means 230 may be a photomultiplier, a semiconductor photodiode, or an array of such detectors. In embodiments other than a CCD, an array is generally preferable to a single detector for some purposes. With an array of small detectors, the user can determine that the maximum fluorescence is being detected and is not inadvertently missed due to misalignment of the collection and detection optics. Optionally, a grating spectrograph is coupled to the CCD or other detection means to provide spectral analysis of the detected light. In that case, means are also provided to integrate the signal function around each peak to determine the total collected fluorescence from a sample. Alternatively, in an embodiment for use in a setting such as in a testing laboratory, and for which all the parameters of the assay have been standardized, the spectrograph may be replaced by a filter which passes only wavelengths in the region of tracer fluorescence.

As is better seen in FIG. 9, waveguide 164 is embodied as a planar portion of a waveguide having at least one planar surface 172 spaced from a second surface 174 by a width 173. At least one surface 174 is disposed in contact with a sample solution 238. Capture molecules 240A, 240B, 240C are immobilized on the exposed surface 172 of the waveguide. In one embodiment, the sample solution 238 contains a plurality of analyte molecules 242A, 242B, 242C of a selected analyte which also includes tracer molecules 244A, 244B, 244C. The tracer molecules can be incorporated into the sample solution by, for example, admixing them with the sample solution before incorporation into the assay or by "drying" the molecules onto the waveguide surface without actually chemically binding them to the surface 172 (or at least not binding them permanently, as would be the case when the tracer molecules are associated with the surface by use of a water-soluble component (e.g., a soluble sugar that does not interfere with the particular interaction between capture and tracer molecules)). The capture molecules 240A, 240B, 240C are chosen or constructed to bind to a binding moiety present on each of the analyte molecules 242A, 242B, and 242C. The tracer molecules 244A, 244B, 244C are chosen to be complementary (in a binding sense) with their respective capture molecules and are constructed to emit fluorescent light in response to stimulation by light of the appropriate wavelength (e.g., by tagging the capture molecule with a fluorescent label). As is more thoroughly described herein, the level of fluorescence emitted by the tracer molecule is a measure of the amount of analyte bound to the capture molecule and is thereby reflective of the concentration of the selected analyte molecule in the solution.

When light beam 218 is being propagated in the waveguide 164 and internally reflected at the surfaces 172, 174, an evanescent light field is produced having an intensity curve 246 which drops off with distance from the surface 172, as diagramed, relative to a distance axis 232 and a horizontal axis (not to scale). Evanescent light intensity varies along axis 232, co-linear with distance. An excitation zone 236 is the only region of the solution in which the evanescent light intensity is sufficient to excite a significant or detectable fraction of tracer molecules 244 (not to scale). Tracer molecules 244 outside zone 236 will contribute little or no induced fluorescence. Excitation zone 236 is typically between about 1000 and 2000 Å in depth.

Capture molecules 240A, 240B, 240C are reactive with the analyte molecules 242A, 242B, and 242C, and may be whole antibodies, antibody fragments such as Fab' fragments, membrane receptors, nucleic acid probes, mixtures thereof, and other molecules which the particular analyte. For instance, capture molecules 240A, 240B, and 240C may also be a receptor molecule of the kind usually found on a cell or organelle membrane and which has specificity for a desired analyte, or a portion thereof carrying the analyte-specific-binding property of the receptor.

The capture molecules 240A, 240B, and 240C may be immobilized on the surface 172 by any method known in the art. However, in the preferred embodiment, the capture molecules are immobilized in a site-specific manner. As used in this application, the term "site-specific" means that specific sites on the capture molecules are involved in the coupling to the waveguide, rather than random sites as with typical prior art methods. Int'l Publ. No. 94/27137, which has been previously referenced, details methods for site-specific immobilization of capture molecules to the surface of the optical substrate by means of a protein-resistant coating on the substrate.

FIG. 9 also stylistically illustrates simultaneous wavelength- and spatially-resolved detection of fluorescence emitted from a waveguide sensor using different capture molecules (Capture $Ab_1$ 240A, Capture $Ab_2$ 240B, Capture $Ab_3$ 240C, ... Capture $Ab_x$), tracer molecules (Tracer $Ab_1$, Tracer $Ab_2$, Tracer $Ab_3$, ... Tracer $Ab_x$), and labels ($F_1$, $F_2$, $F_3$, ... $F_x$) with the purpose of detecting different analytes of interest ($Analyte_1$ 242A, $Analyte_2$ 242B, $Analyte_3$ 242C, ... $Analyte_x$) in a sample solution 238.

In the depicted embodiment, the device works as otherwise herein described, but each tracer molecule (e.g., Tracer $Ab_1$, Tracer $Ab_2$, Tracer $Ab_3$, ... Tracer $Ab_x$) is labeled with a different colored flourophore ($F_1$, $F_2$, $F_3$, ... $F_x$).

The waveguide is illuminated by one or more different wavelengths of light beam 218 appropriate to excite all the fluorophores located within the evanescent region of the waveguide. In one configuration, the emissions from the different fluorophores are distinguished using bandpass filters. Light rays 248, 249 and 250 are emitted from the respective labels on the tracer molecules. This light then passes through a lens 252 which collimates the emitted light onto a band pass filter 254 selective for the wavelength emitted by the particular tracer molecule label, in the depicted case, Tracer $Ab_1$. A filter switching member, such as a wheel 256, houses, for example, three different band pass filters—each selective for a different fluorophore label. Thus, only the light rays 248 emitted by Tracer $Ab_1$ pass through the filter 254. If spatial resolution is desired in addition to wavelength selection, the light 248 passing through the filter 254 passes through a second lens 258 which images the light 248 onto a spatially-resolved photodetector 260 such as a CCD or diode array. If only wavelength resolution is desired, the photodetector 260 may be a single spatially-integrating device, and lens 258 may be optionally omitted.

Alternatively, the wavelength selectivity may be accomplished by one of several means instead of a filter wheel, such as employing a diffraction grating, a prism, or an acousto-optical modulator to angularly separate the different emitted wavelengths and thus direct them to separate individual photodetector elements whose outputs are representative of the signal strengths in each wavelength band. In another arrangement which avoids the use of the rotating filter wheel, stationary beam splitters are employed to direct portions of the emitted light through stationary filters placed in front of individual photodetector elements.

Alternatively, if the excitation wavelengths of the different fluorophores are sufficiently separated without appreciable overlap, the light source may sequence in time through each excitation wavelength. The emitted light at any given time is related to the signal strength of the fluorophore set whose excitation wavelength is chosen at that particular time, and no further wavelength selective devices, such as filters, are needed.

The waveguide can be designed so that multiple (e.g., four) different assays can be performed on the same sample. This is accomplished by immobilizing different types of capture antibodies on different regions of the waveguide, a process referred to as patterning. Three different patterning methods appear suitable for immobilizing antibodies to the polystyrene sensors—gasketed multi-well coating tray, liquid jet printing and photolithography. In the second, a machine similar to an "ink jet" printer is used to spray reagents onto a specific region of the waveguide; in the last, ultraviolet light is used to photochemically cross-link antibodies to selected regions.

One immobilization chemistry is based on physical adsorption of antibodies to the waveguide. In one method, an antibody is briefly exposed to acidic conditions just prior to immobilization. It has been shown that this acid pretreatment step improves the antigen-binding capacity ("AgBC") of immobilized antibodies by up to 3-fold in some cases. This immobilization chemistry is relatively simple and compatible with gasketed multi-well coating tray or liquid jet printing technology, but in some cases it exhibits a higher degree of non-specific binding than other methods.

The other two immobilization chemistries are based on a family of tri-block polymers of the form PEO-PPO-PEO, where PEO stands for poly(ethylene oxide) and PPO stands for poly(propylene oxide). These surfactants are sold under the trade designation PLURONICS® and come in a variety of chain lengths for both the PEO and PPO blocks. The PPO block is significantly more hydrophobic than the PEO blocks and adsorbs readily to non-polar surfaces such as polystyrene, leaving the PEO blocks exposed to bulk solution. The free ends of the PEO chains exhibit high mobility, literally sweeping proteins away from the surface.

In both the second and third immobilization chemistries, the surface of the waveguide is coated with pluronics before attachment of antibodies, but the two chemistries differ in how the antibodies are attached. In the second chemistry, a photochemical cross-linking agent is used to conjugate antigen-binding fragments (Fab') to the PEO blocks, making this method suitable for patterning by photolithography. In the third chemistry, Fab' fragments are attached to pluronics using a chemical cross-linking agent, making this method compatible with gasketed multi-well coating tray or liquid jet patterning. The photochemical cross-linking method was evaluated with two different PLURONICS® (F108 & P105) and two different photochemical crosslinkers (BPM and BPIA). While acceptable levels of total antigen binding can be obtained with all four pairwise combinations, an unacceptable level of NSB (Non-Specific Binding) may be obtained when antibodies are immobilized to F108 using the BPIA crosslinker. The other three pairwise combinations give very low levels of NSB (about 1.5% of total binding). Furthermore, the P105/BPM pair is especially good, giving an undetectable level of NSB.

In FIG. 9, a sandwich immunoassay scheme is depicted. See, e.g., U.S. Pat. Nos. 4,376,110 and 4,486,530 to Hybritech, Inc. However, as will be apparent to the skilled person, alternate assay schemes such as displacement assays may adapted to be performed with the invention.

In tests conducted with the point-of-care cardiovascular marker CK-MB (associated with acute myocardial infarction) on both plasma and whole blood, the results were comparable (taking into consideration diffusion and viscosity differences).

In the embodiment of the apparatus of FIG. 8, measurements of fluorescence are made by spectroscopy. Fluorescence detection may be performed with a monochromator (SPEX Industries, Inc., Model 1680C) and a CCD (Photometrics Ltd. Series 200, or CH-250). Alternatively, light source 216 can be any light source emitting at the wavelength desired for excitation of selected fluorescent dyes. Also, once an assay procedure has been validated and standardized, it may not be necessary to measure the fluorescence spectrum or spatial distribution of fluorescence. The detection means may be simplified in accordance with the minimum requirements of the assay.

In another alternate embodiment, light source 216 is a laser diode emitting in the red wavelength region of 600–700 nm which is commercially available. The laser diode may provide about 12 milliwatts of power with a peak emission wavelength of about 635 nm. Laser diodes emitting at 633 nm are also available and can be used. For an embodiment using a wavelength in this region, it is necessary to use dyes such as cyanine dyes, whose fluorescence can be stimulated by excitation with wavelengths in the red spectral region. An example of such a dye is the fluorescent dye Cy5, available from Biological Detection Systems, Inc., Pittsburgh Pa. (catalog no. A25000). The Cy5 dye can be conjugated to the desired tracer molecule by the manufacturer's instructions and/or with a kit available from BDS. A second dye, Cy7, may also be suitable. The dyes and methods for conjugating are also characterized in the paper by Southwick, P. L., et al., titled "Cyanine Dye Labelling Reagents—Carboxymethylindocyanine Succinimidyl Esters", *Cytometry* 11:418–430 (1990). The use of laser diodes as a light source permits the biosensor and waveguide to be formed of plastic, which considerably reduces the expense of manufacture and facilitates the integral molding of the semi-cylindrical lens with the waveguide and reservoirs.

Different labels can be used which emit light at different wavelengths if desired. In such a circumstance, different types of capture molecules (e.g., antibodies reactive with different antigens) can be immobilized to the surface so that the waveguide can be used to detect more than one molecule to be detected. In such a case, multiple wavelengths can be detected by multiplexing the signal from the waveguide.

F. Chemistry

Cardiac markers for use with the present invention will generally include "ischemic markers" (e.g., myosin light chain I, myosin light chain II, and tropomyosin), markers released from cardiac tissue only after a myocardial infarction (e.g., myoglobin, LDH, and serum glutamic oxalacetic transaminase("SGOT")), and "cardiac specific markers" (e.g., troponin I, troponin T, CK-MB (a myocardial isoform of creatine kinase), and glycogen phosphorylase BB). See, e.g., U.S. Pat. No. 5,604,105, issued Feb. 18, 1997 to Jackowski, at col. 10, line 39 to col. 11, line 10 and col. 18, line 5 to col. 19, line 18 for an identification of particular markers, and the remainder of the Jackowski patent for a thorough discussion of such markers in general.

In a particularly preferred embodiment (especially useful when myoglobin is one of the markers used in the assay), unlabeled tracer antibody may be added to the reaction chamber to dampen the amount of fluorescence after the presence of the analyte has been determined. For example, in an assay wherein a low sensitivity antibody to myoglobin is used in one assay zone, and a relatively higher sensitivity antibody to troponin-I is used in a second assay zone on the waveguide proximal the portion where the anchoring antibodies for myoglobin are present, unlabeled tracer antibody may be added at some time during the performance of the assay to the liquid phase to dampen the amount of fluorescence occuring from the myoglobin assay zone.

G. Analysis

The concentration of a cardiac marker is determined by a flexible time assay consisting of a rapid assay which measures the high concentration analyte faster than the lower concentration analytes. Such a rapid assay can be utilized because patients suffering from acute myocardial infarctions have elevated levels of the cardiac marker proteins in their blood. For such elevated levels, less reaction time is required to achieve a given precision in the assay determination.

Determination of cardiac marker presence may be achieved by utilizing a flow cell assembly 190 (FIGS. 4, 10, and 11), as described in the present disclosure. An assay test solution (i.e., the patient's whole blood, plasma, diluents, or mixtures thereof) is introduced into the flow cell assembly or biosensor 190. Immediately after the flow cell assembly 190 has been filled with test solution, the assay time "t" is considered to be zero, and the first or "zero" measurement of fluorescence intensity from each designated binding area containing selected capture molecules on the waveguide 164, such as capture molecules 240A, 240B, and 240C illustrated in FIG. 9, is taken by the light detection means 230 (FIG. 8). At subsequent, substantially equally spaced points in time, additional fluorescence intensity measurements are taken by the light detection means 230. After each of these measurements, the entire group of data for a given designated binding area (i.e., the zero measurement through the most recent measurement inclusive) is analyzed as the fluorescence readings being a function of time. The increase in fluorescence intensity with time is related to the binding kinetics of the assay which is, in turn, related to the concentration of the target analyte. The analysis of fluorescence reading versus time is performed using a least squares curve fitting routine which calculates curve fit model parameters, as well as the standard and relative errors of the curve fit parameters. The general curve fitting model used is related to a pseudo-first order binding rate equation and is as follows:

$$F = R \times [\{1-\exp(-k \times t)\}/\{k \times \exp(-t_R \times k)\}] + I_o$$

where:

F is fluorescence intensity reading from the assay device.

R is the rate parameter.

k is a mass transport constant that reflects the geometry of the reaction chamber, the rheology of the sample fluid, and the association constant of the antibody.

$t_R$ is a time parameter fixed at 2.5 minutes.

$I_o$ is the model parameter denoting the y intercept of the model.

t is the time after the beginning of the assay.

The $t_R$ set at 2.5 minutes because it is one-half the standard assay duration of 5 minutes. Since the reaction rate changes with time, the slope of the curve changes continuously. A point in time must be chosen, in this case 2.5 minutes, to normalize the assay curve to a standard curve.

If the value of k is not fixed, this model is nonlinear and must be fit using a general nonlinear curve fitting procedure to determine the model parameters. This requires a lengthy procedure to calculate the standard and relative errors for the curve fitting parameters. It has been found the value of k can be fixed without introducing additional significant error into the final curve fit. The value of k doesn't generally vary with concentration of the analyte of interest. The value of k was determined by allowing k vary during the early stages of the curve fitting analysis. Having observed the value of k over various concentrations, it was found that it varied only nominally and was fixed to a value. For example, the value of k to determined as 1.5 min$^{-1}$ for myoglobin, 1.5 min$^{-1}$ for CK-MB, and 0.4 min$^{-1}$ for troponin I.

Therefore, with the values of k was and $t_R$ fixed, the model becomes $F = R \times Z + I_o$ where Z is the $[\{1-\exp(-k \times t)\}/\{k \times \exp(-t_R \times k)\}]$ portion of the original model equation, but is only a function of t (time). Thus, the model is linear with respect to the curve fit parameters. This simplification allows for the use of general linear curve fitting methods and equations that follow:

$$R = (\Sigma[(Z_i - Z_{mean})(F_i - F_{mean})])/(\Sigma[Z_i - Z_{mean}]^2)$$

$$I_o = F_{mean} - R \times Z_{mean}$$

Standard Error of $R = [\Sigma(F_i - F_{predicted})^2]^{1/2}/(n-2)^{1/2}/[\Sigma(Z_i - Z_{mean})^2]^{1/2}$ Relative Error of R = (Standard Error of R)/R where:

subscript "i" is one of the data points (e.g., i=1 (1$^{st}$ fluorescence measure), 2 (2$^{nd}$ fluorescence measurement) . . . , and x (last fluorescence measurement)).

subscript "mean" is the mean value over all data points collected.

subscript "predicted" is the predicted value from the model.

$\Sigma$(summations) are over all data points.

After a minimum assay time (determined by the reading interval and the reading noise (such as "shot" noise and temperature variation in the CCD) of the assay system), the relative error value of R is used to determine if the curve fit data are adequate to predict a target analyte concentration based on the R (rate) curve fitting parameter. When the relative error of R has dropped below an acceptable threshold, the value of R can be used along with an assay standard curve (correlating R to target analyte concentration) to ascertain the concentration of the target analyte assay. The assay can then be ended, if desired, or allowed to continue its run. The minimum assay time is controlled by two parameters, the douche cycle of the system and the data acquisition cycle (usually 15 seconds of the present system). Further, a minimum of 4 readings must be taken.

Preferably, a computer having appropriate software operates the entire assay device, calculates (solves the curve fitting equations), correlates, and records the incoming data. Once a predetermined concentration level of the cardiac markers of interest is detected or after a certain duration of time (for situations where no cardiac markers of interest is detected), the computer sets off an alarm, or otherwise reports back to the user. It is anticipated that standard curves will be constructed for each analyte interest to be assayed, preferably constructed for each batch of waveguides coated with capture molecules.

The invention is further explained by the following illustrative examples.

EXAMPLES

Example I

A waveguide with integrated lenses, such as that depicted in FIGS. 6 & 7, was injection molded in a clean environment from a transparent, general purpose polystyrene. The waveguide had a length of 38 mm, and a width of 25 mm. The thickness 173 of the planar surface 170 was a consistent 0.5 mm. The ridge or "shelf" 176 had a height of 1.3 mm. The front lens and rear lens had bottom edges co-planar with their respective centers of curvature. The front lens horizontal angle 262 was about 15°. The rear lens horizontal angle 264 was about 19°. The radii of curvature of the front and rear lenses were about 3.2 mm and 1.6 mm respectively. The mean angle of the front lens was 21°. The mean angle of the rear lens was about 24°.

Example II

A flow cell top 100, such as that depicted in FIGS. 1–3, and 10, was made of hard black anodized 6061-T6 aluminum. It contained three reservoirs, each of which had a 0.25 mm (0.010 in.) thick wall surrounding it, a flat floor in the middle, two half-capsule shaped recesses at either end 1.6 mm (1/16 in.) in width, and ports 1.6 mm (1/16 in.) in diameter running into the center of each recess. The ports opened into a #10-32 (standard thread, not NPT) connector which ran out to the opposite face of the flow cell and was 5.1 mm (0.200 in.) deep. A 90° countersink 266 (FIG. 2) was given at the surface of the port connector (a plastic barbed tubing connector screwed into the port connector and sealed on the countersink). On both sides of the array of reservoirs were two raised platforms which were referred to as lands 268, 270. Each land had three holes running through the thickness of the part. The four #31 clamping holes 272, 274, 276, 278 were formed (i.e., drilled through). The two apertures 178, 180 were drilled and reamed to achieve a close sliding fit with 2.4 mm (3/32 in.) nominal four-sided registration pins 182, 184 press fit into the second frame member 186.

Example III

A gasket 162, such as that depicted in FIGS. 4 and 5, was made as a composite structure laminated from 1.6 mm (1/16 in.) silicone rubber sheeting and 0.076 mm (0.003 in.)

self-adhesive FEP film (total thickness: 1.676 mm (0.066 in.) nominal). Its outer dimensions were about 25 mm (1 in.) by 25.40 mm (1.000 in.) and it had three internal openings which corresponded to the flow cell reservoirs. The gasket was produced using a waterjet cutter and was seated on the flow cell such that the FEP layer faced away from the flow cell surface.

Example IV

Figure 10:
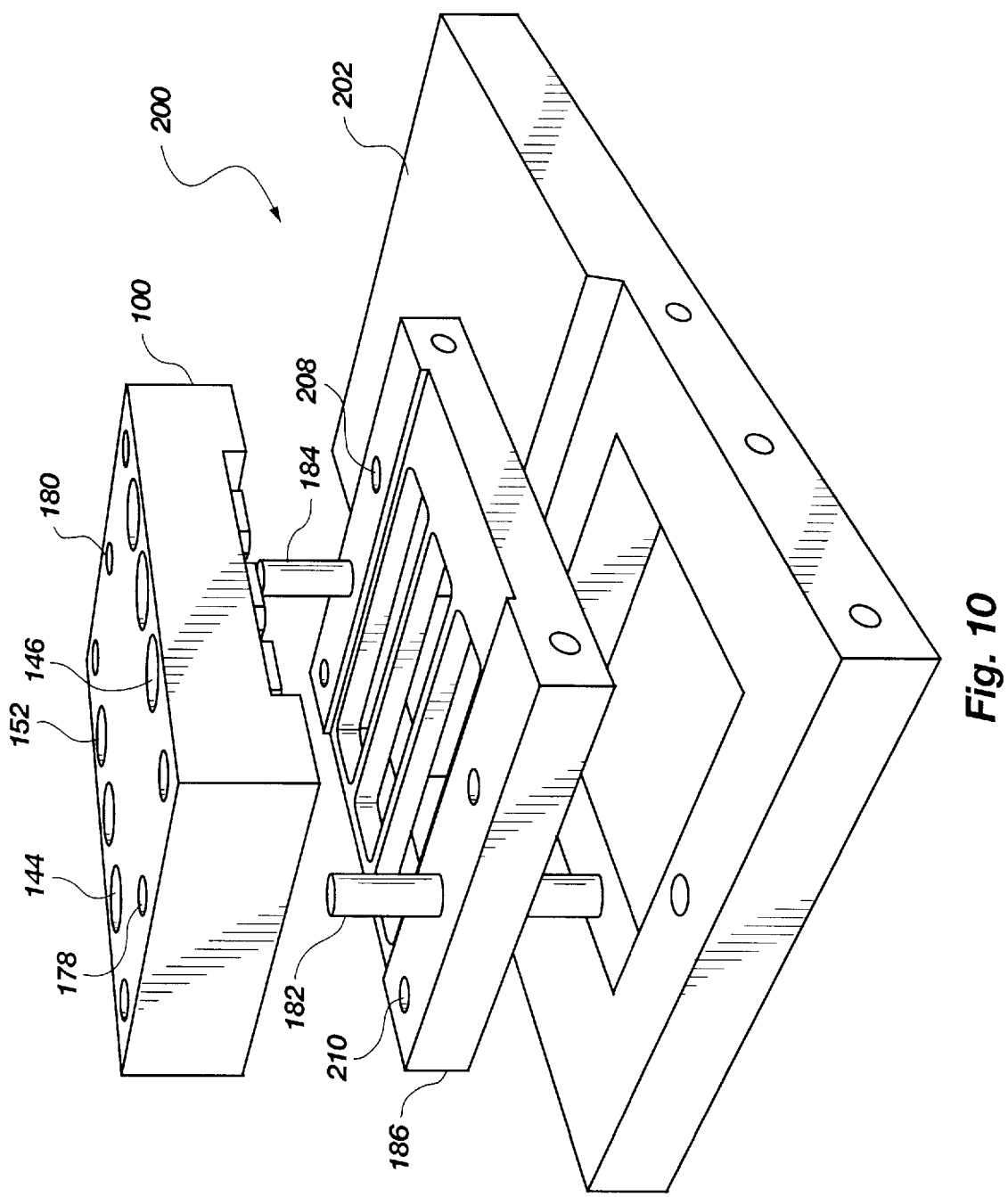
FIG. 10 depicts an enlarged, exploded, perspective view of the flow cell portion of a biosensor for use with the invention.

A second frame member 186, such as that depicted in FIGS. 4, 10 and 11 was made from hard black anodized 6061-T6 aluminum. It contained three internal openings 280, 282, 284 which corresponded to the three reservoirs 102, 104, 106 of the flow cell 100 (but were slightly longer). The internal openings were positioned in a shallow depression (0.46 mm (0.018 in.) deep) 286 which seated the waveguide, and allow evanescent light emitted from any reacting tracer molecules on the waveguide surface to be detected by the detection means 230. As with the flow cell top 100, two lands 288, 290 resided on either side of the internal openings, each land having three holes. Four clamping holes (e.g., 208, 210) were drilled through and tapped to #4-40 to receive thumb screws. Two apertures were drilled through to receive a 3.2 mm (⅛ in.) nominal dowel which was press fit into the hole. The dowel was stainless steel and projected approximately 7 mm (0.280 in.) above the top surface and 6.6 mm (0.260 in.) below the bottom surface of the second member. The exposed dowel was machined down to 2.4 mm (3/32 in.) nominal diameter and was squared off to produce a low-friction locating registration pin 182, 184. The bottom aspect of the secondary member was milled out to provide a single large window 292 for emitted fluorescence from the waveguide. The front surface of the secondary member contains two mounting holes 294, 296 #2-56 drilled and tapped to a depth of about 4 mm (0.15 in.) to fasten the waveguide registration plate 212. The registration plate is a simple U-shaped bracket which was produced from 1.6 mm (1/16 in.) nominal 6061-T6 aluminum plate. It contained two #42 holes which corresponded to the holes on the front of the second member. The purpose of the registration plate was to provide a lateral hard-stop for the waveguide during clamping into the flow cell. The upright arms of the part contact the waveguide at the outer edges of the input coupling lens while allowing unimpeded coupling with the incoming laser beam.

Example V

A flow cell stage 202 (FIG. 4) is a plate-like structure which was made from hard black anodized 6061-T6 aluminum. The receiving site 298 of the part was down-stepped and contains a single rectangular internal opening. Three #2-56 drilled and tapped holes 300, 302, 304 were positioned on the front of the part which were used to fasten a laser beam mask (not shown). Two #10-32 holes 306, 308 were drilled to a depth of 19 mm (0.750 in.) on the right side of the part to mount the stage to the test apparatus. The internal opening had beveled front 310 and rear 312 sides. Located on either side of the window were two 2.4 mm (3/32 in.) apertures (analogous to those in the flow cell) which allowed the clamped flow cell and second member to be mounted to the flow cell stage 202.

Example VI

The waveguide and integrated lenses of EXAMPLE I, the flow cell top of EXAMPLE II, the gasket of EXAMPLE III, the second member and registration plate of EXAMPLE IV, and the flow cell stage of EXAMPLE V were associated, as in FIG. 4. A hard, black anodized coating was added to the parts with a nominal build-up of 0.0025 mm (0.001 in.), however, the flow cell assembly or biosensor 190 was checked, as much as possible, prior to anodization to maximize the probability of proper fit.

The gasket was cut to correspond to the outside dimensions of the three reservoirs 102–106 of the flow cell top 100. The silicone rubber surface contacted the flow cell and the FEP surface contacted the waveguide when the assembly was clamped. Any flash present on the gasket which interfered with seating or which came over the top of the walls was carefully trimmed back with a razor knife (the top of the dam was exposed to the surface of the waveguide, but did not touch it; flash from the gasket can interfere with proper clamping).

The waveguide 164 was seated in the shallow depression in the second member 186. The waveguide fit into the depression with minimal lateral movement, but without compression or pinching. A small amount (e.g., less than about 0.1 mm (0.003 in.)) of lateral movement was acceptable. If pinching occurred, additional milling to the walls of the depression was necessary to allow proper seating.

To insure that the waveguide 164 was reproducibly positioned directly beneath the flow cell, it was butted up against the registration plate 212 after being seated in the secondary member 186. Contact with the registration plate 212 was only at the outermost corners of the front lens; no contact with the injection mold stub on the underside of the front lens occurred (injection mold may be designed to place resultant stub at an alternate location). The front of the second member may need to be milled to ensure the waveguide sits directly beneath the flow cell when in contact with the registration plate.

After seating the gasket into the flow cell and positioning the waveguide on the second member, the flow cell was mated with the second member by engaging the locating pins into the apertures in the flow cell. When fully engaged, but without adding additional clamping force (i.e., the gasket was not compressed), there was a 0.15 mm (0.006 in.) gap between the lands of the flow cell and the lands of the second member. When fully clamped with four thumb screws such that the lands are in contact, the gasket is compressed 0.15 mm (0.006 in.). The flow cell and second member readily separated using manual force; no sticking occurred, but a thin coat of lubricant may be used on the pins, if necessary. It may be desirable to slightly countersink the press fit hole on the second member and/or the aperture on the flow cell to avoid burrs or bulges which might impair mating of the two parts.

The locating pins from the bottom of the second member readily aligned and fit into the apertures on the stage. No perceptible play existed between the parts when mated. As with the flow cell and second member fit, the second member and stage readily separated using moderate manual force.

Example VII

A waveguide with integrated lenses as seen in EXAMPLE I, was used treated with monoclonal antibodies directed against myoglobin (available from Genzyme Corp. of San Carlos, Calif., USA)) were coated (a first coating of 1 ml per waveguide of 5 e $^{-8}$M, followed by a second coating of BSA/sugar solution)) onto a first assay zone of the waveguide to serve as capture molecules for myoglobin which might be present in the sample to be analyzed. Similar antibodies directed against myoglobin were labeled with Cy5 dye tracer for use in the liquid phase.

Figure 14:
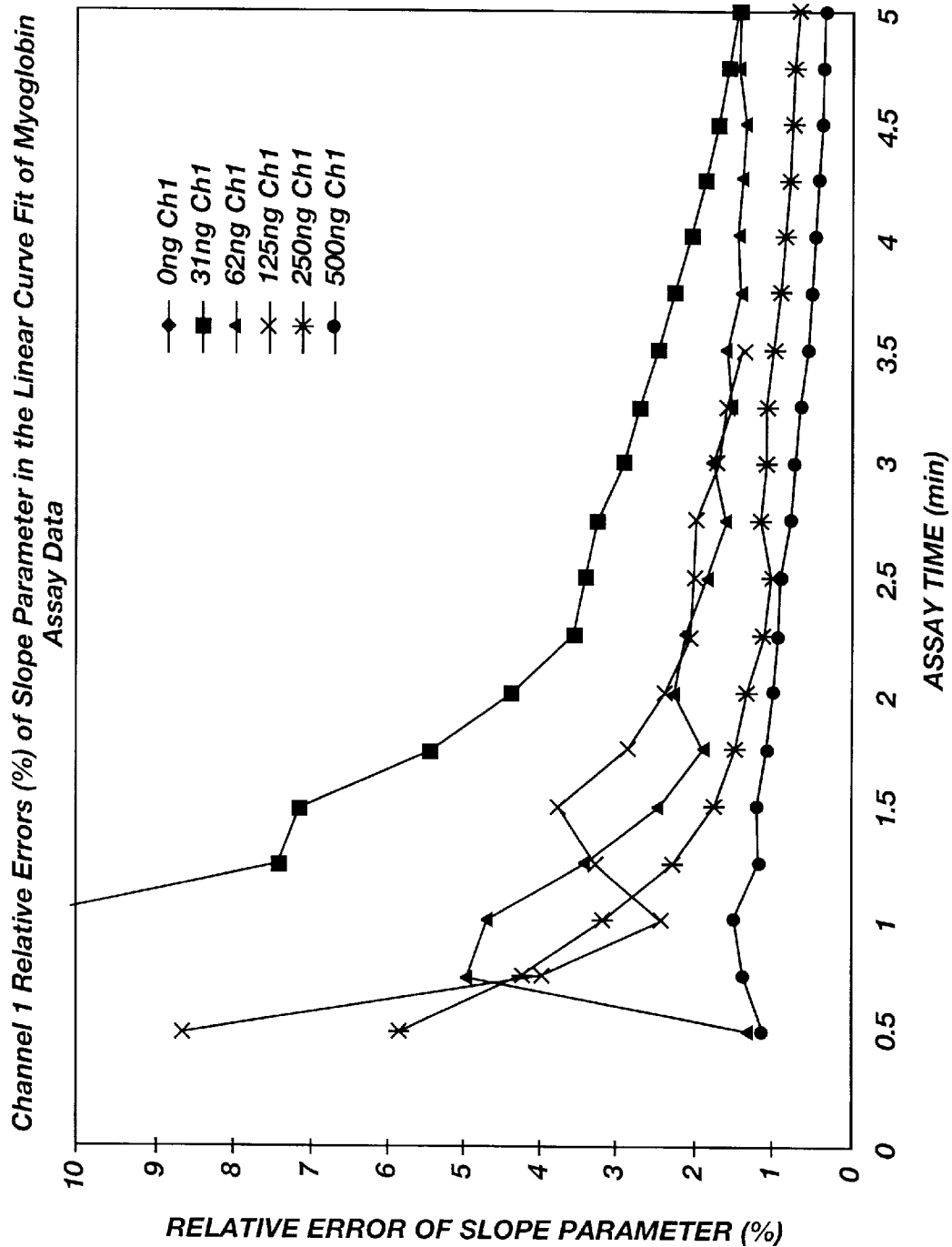
FIG. 14 is a graph of relative errors (%) of slope parameter in a linear curve fit of myoglobin assay data.
Figure 15:
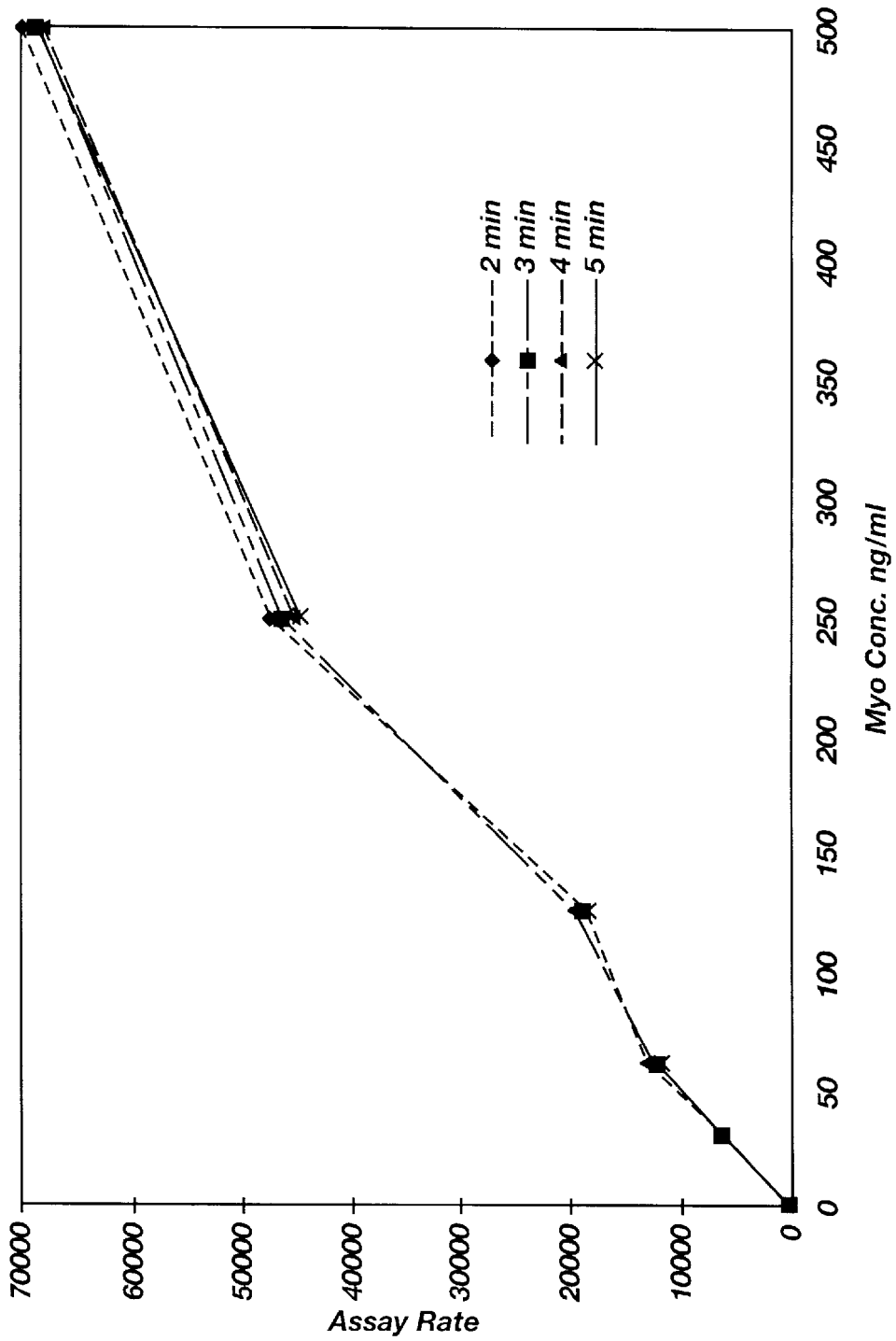
FIG. 15 is a graph of a standard curve calculated by linear regression of assay rate versus myoglobin concentration for various time durations.

The waveguide was attached to the flow cell assembly (see FIG. 8) and various concentrations of myoglobin in solution (i.e., 0 ng/ml, 31 ng/ml, 62 ng/ml, 125 ng/ml, 250 ng/ml, and 500 ng/ml) were introduced into the flow cell assembly. Fluorescence readings were taken every 15 seconds for 5 minutes. As it can be seen from FIG. 14, the relative errors (%) of the slope parameter in the linear curve fit, as calculated by the equations given above, are below 5% after 2 minutes of assay time for each of the various concentrations. Thus, accurate concentration determinations should be achieved after 2 minutes. This is verified in FIG. 15, which is a graph of the standard curve calculated by the above linear regression equation of assay rate versus myoglobin concentration for various time durations (i.e., 2 minutes, 3 minutes, 4 minutes, and 5 minutes). As it can be seen from FIG. 15, the assay rates determine for each concentration varied only slightly through the time durations. Thus, a determination of assay rate from the fluorescence reading will yield an accurate concentration determination after only 2 minutes.

Example VIII

A waveguide with integrated lenses as seen in EXAMPLE I, was used treated as follows:

A. First Assay Zone (Troponin-I assay):

Monoclonal antibodies directed against Troponin I Peptide 4 (cardiac TN I, N-terminus left, -RGEKGRALSTRCQPLELA- (available from Fortron Bio Science, Inc. (Morrisville, N.C., USA) (no preservatives added)) were immobilized (a first coating of 1 ml/waveguide at 5 e −8M, followed by a second coating of BSA/sugar solution)) onto the first assay zone of the waveguide of EXAMPLE I to serve as capture molecules for Troponin-I which might be in the sample to be analyzed. The antibodies were directly absorbed onto the first assay zone, and post-coated with human serum albumin.

Similar antibodies (available from Genzyme Corp. Of Cambridge, Mass., US) directed against Troponin I Peptide 3 (cardiac TN I, N-terminus left -RAYATEPHAKKKSKISASRKLQIXTLLLQIAKQ-) (5 e $^{-}$9M) were labeled with Cy5 dye tracer for use in the liquid phase (as "tracer").

B. Second assay zone (CK-MB assay):

Monoclonal antibodies directed against CK-MB (J. Ladenson, *Clinical Chemistry*, 32:657–663 (1986)) were immobilized (from Washington University in St. Louis, Mo., US) onto the second assay zones of a waveguide for use as capture molecules. Similar antibodies directed against CK-MB were labeled with Cy5 dye tracer for use in the liquid phase. Recombinant CK-MB is available from Genzyme Corp. of San Carlos, Calif., US.

C. Third Assay Zone (Myoglobin (16,900 MW) assay):

Monoclonal antibodies directed against myoglobin (available from Genzyme Corp. of San Carlos, Calif.) were immobilized (a first coating of 1 ml/waveguide at 5 e $^{-}$8M followed by a second coating of BSA/sugar solution)) onto the third assay zones of the waveguide to serve as capture molecules for myoglobin which might be present in the sample to be analyzed. Similar antibodies directed against myoglobin were labeled with Cy5 dye tracer for use in the liquid phase.

In the waveguide, Channel 1 had the clinical sample, Channel 2 was the reference solution (or buffer), and Channel 3 was a high standard.

Example IX

Figure 16:
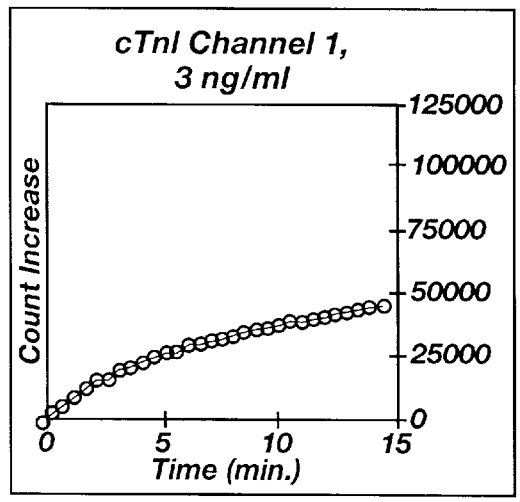
FIG. 16 illustrates graphs of the assay results for three different channels for troponin I in a single assay, plotted as fluorescence detected (Count Increase) as a function of time.
Figure 16:
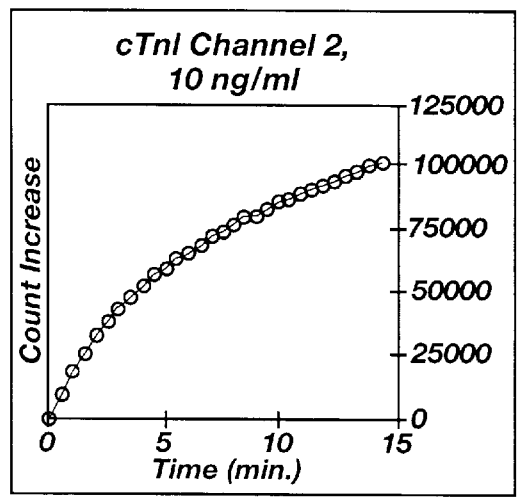
Figure 16:
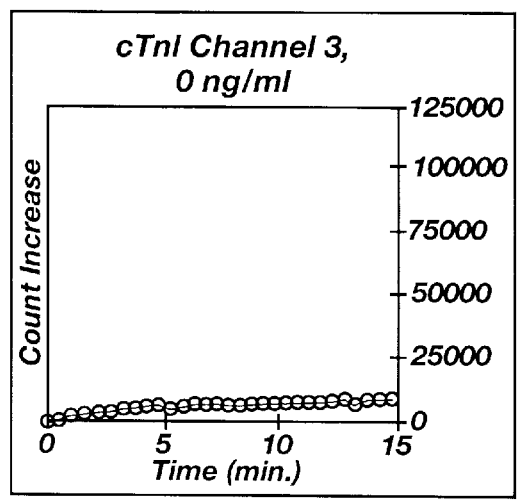
Figure 17:
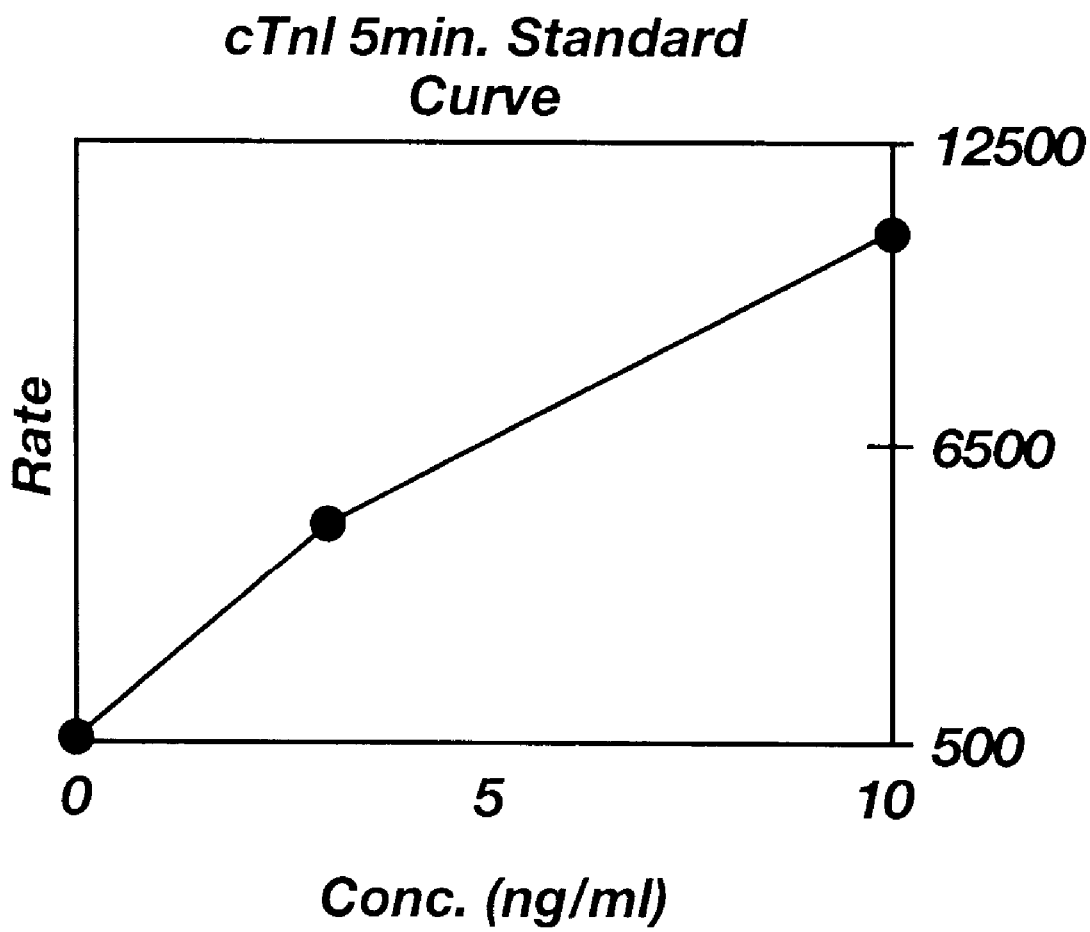
FIG. 17 is a graph of a standard curve calculated by linear regression of assay rate versus troponin I concentration for various time durations.
Figure 18:
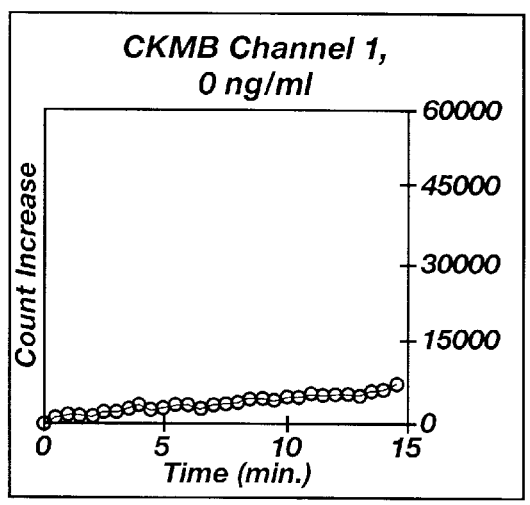
FIG. 18 illustrates graphs of the assay results for the three different channels for CK-MB in a single assay, plotted as fluorescence detected (Count Increase) as a function of time.
Figure 18:
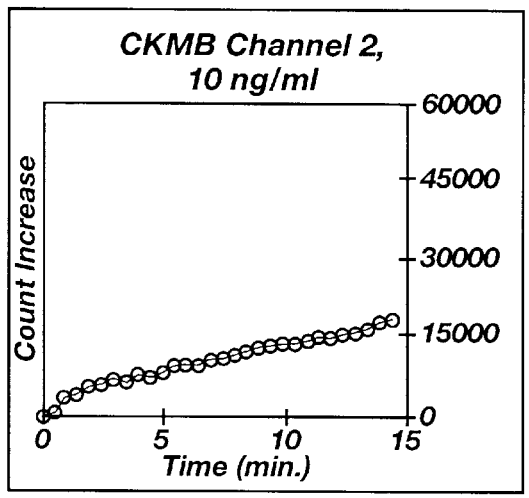
Figure 18:
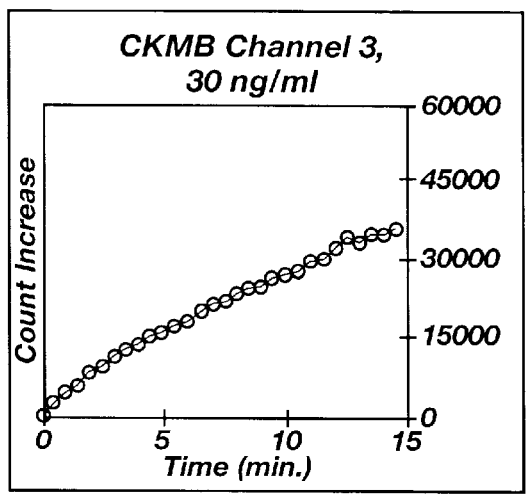
Figure 19:
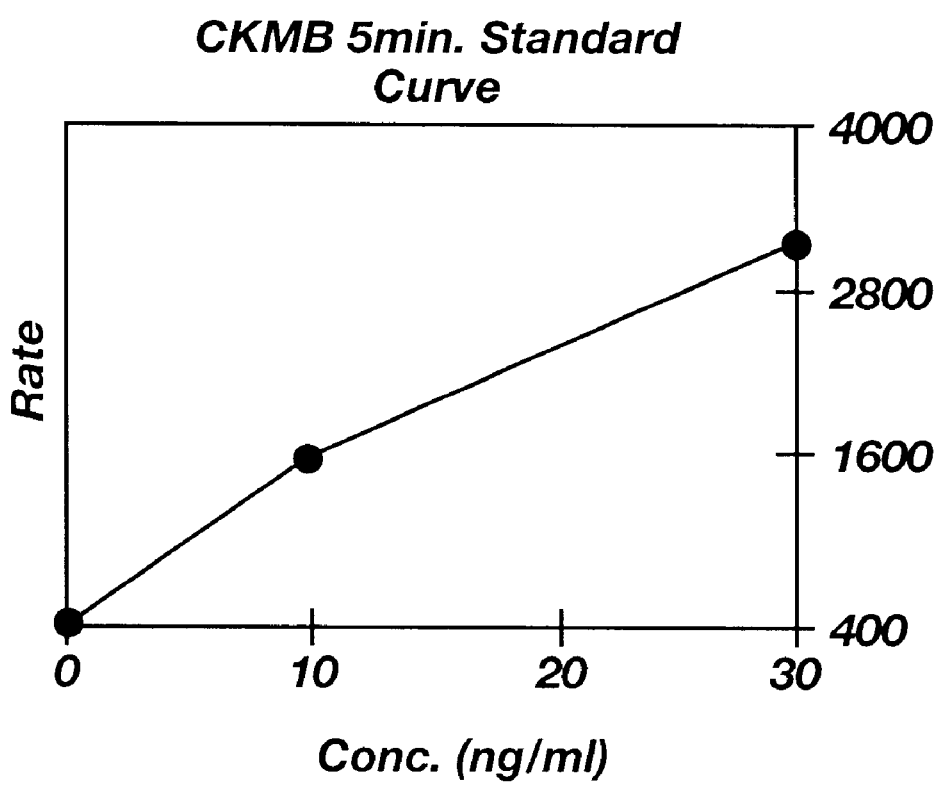
FIG. 19 is a graph of a standard curve calculated by linear regression of assay rate versus CK-MB concentration for various time durations.
Figure 20:
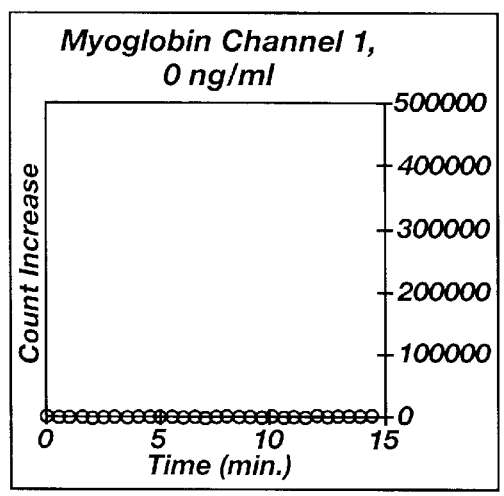
FIG. 20 illustrates graphs of the assay results for three different channels for myoglobin in a single assay, plotted as fluorescence detected (Count Increase) as a function of time.
Figure 20:
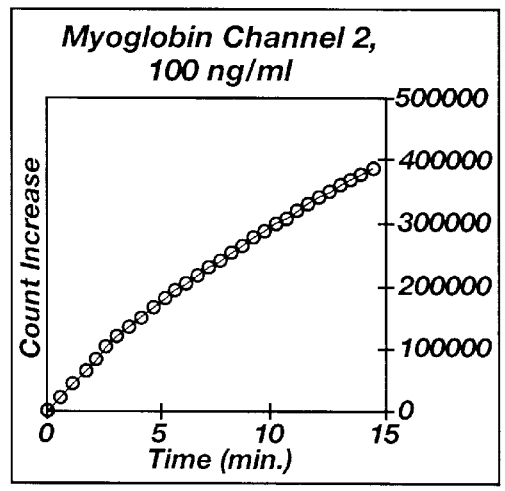
Figure 20:
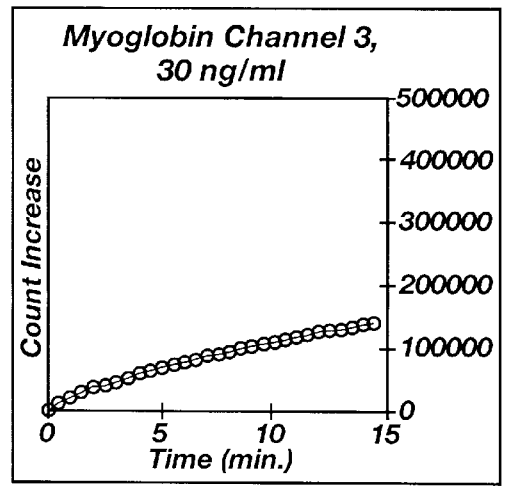
Figure 21:
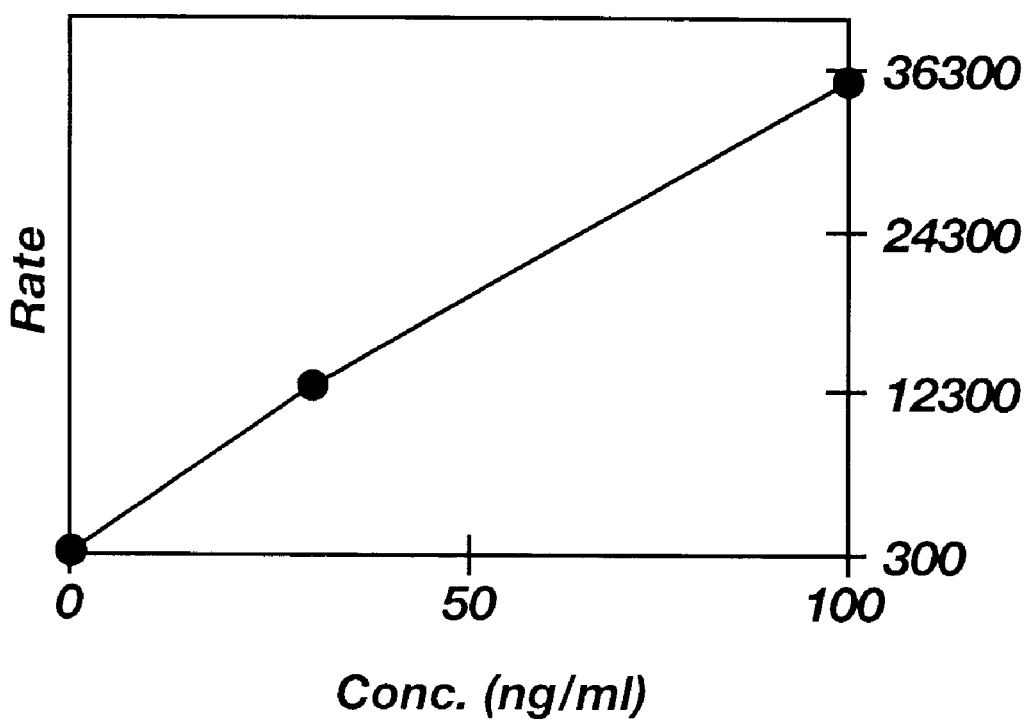
FIG. 21 is a graph of a standard curve calculated by linear regression of assay rate versus troponin I concentration for various time durations.

The waveguide of the previous EXAMPLE was used in an assay. This assay was developed to simultaneously measure CK-MB, myoglobin and cardiac troponin I in a plasma sample on a single, three flow channel sensor having three sequential assay zones (wherein the third assay zones are closest to the source of light propagation, and the first assay zone is furthest from the source of light propagation, with the second assay zone being placed therebetween). In the first flow channel, troponin I (3 ng/ml) was measured in the first assay zone, CK-MB (0 ng/ml) was measured in the second assay zone, and myoglobin (0 ng/ml) was measured in the third assay zone. In the second flow channel of the sensor, troponin I (10 ng/ml) was measured in the first assay zone, CK-MB (10 ng/ml) was measured in the second assay zone, and myoglobin (100 ng/ml) was measured in the third assay zone. In the third flow channel, troponin I (0 ng/ml) was measured in the first assay zone, CK-MB (30 ng/ml) was measured in the second assay zone, and myoglobin (30 ng/ml) was measured in the third assay zone. The assay results for the three different channels for troponin I is depicted in FIG. 16 (fluorescence detected (count increase) versus time), while the standard curve from these graphs is depicted in FIG. 17 (assay rate versus concentration of analyte). The assay results for the three different channels for CK-MB is depicted in FIG. 18 (fluorescence detected (count increase) versus time), while the standard curve from these graphs is depicted in FIG. 19 (assay rate versus concentration of analyte). The assay results for the three different channels for myoglobin is depicted in FIG. 20 (fluorescence detected (count increase) versus time), while the standard curve from these graphs is depicted in FIG. 21 (assay rate versus concentration of analyte).

A CK-MB threshold of 0.2 ng/ml (in buffer) was established for recombinant CK-MB. Preliminary sensitivity data of 0.2 ng/ml free troponin I antigen (23,500 MW) in plasma was demonstrated.

Characteristics of the described and illustrated embodiments are intended for illustrative purposes, and are not to be considered limiting or restrictive. It is to be understood that various adaptations and modifications may be made by those skilled in the art to the embodiments illustrated herein, without departing from the spirit and scope of the invention, as defined by the following claims thereof.

What is claimed is:

1. A method of performing an assay comprising:
   providing an assay system which receives a biological liquid sample potentially containing at least one analyte of interest and outputs a light signal indicative of the rate of reaction between said analyte of interest and a reactive element within the assay system;
   continuously measuring light emitted from said assay system over time;
   continuously correlating said rate of reaction to a concentration of said analyte of interest; and
   determining the concentration of at least one analyte of interest in said biological liquid sample based on said correlation of said light in a time period less than about five minutes.

2. The method of claim 1, wherein said at least one analyte of interest is an ischemic marker.

3. The method of claim 2, wherein said ischemic marker is selected from the group comprising troponin I, CK-MB, and myoglobin.

4. The method of claim 1, wherein said assay system comprises:
   a light source;
   a biosensor comprising a waveguide having at least one planar surface, said waveguide associated in liquid tight attachment with a first member, said first member, in conjunction with the waveguide, defining at least one reservoir for containing said biological liquid sample, the planar surface of said waveguide being associated in part with capture molecules, and an inlet and outlet in fluid communication with said reservoir for infusing and draining said biological liquid sample into and out of said reservoir so as to allow the biological liquid sample to contact said capture molecules; and a light detector for detecting light passed through said planar surface.

5. The method of claim 4, further comprising:

simultaneously introducing tracers molecules and a biological liquid sample potentially containing at least one analyte of interest into said at least one reservoir of said biosensor, wherein said tracer molecules are complementary with said respective capture molecules and emit fluorescent light in response to stimulation by light of an appropriate wavelength; and introducing a light beam from said light source into said waveguide to propagate light of said appropriate wavelength to stimulation a fluorescent light response in said tracer molecules which have attached to a portion of at least one said analyte of interest which has been captured by said capture molecules on said waveguide planar surface.

6. An assay system for analyzing a biological liquid sample, comprising:

a light source;

a waveguide having at least one planar surface and being optically associated with a rear lens oriented for reading light from said light source passing through said waveguide, to monitor coupling efficiency and beam quality;

a first member associated in liquid tight attachment with said waveguide, wherein said first member, in conjunction with the waveguide, defining at least one reservoir for containing the biological liquid sample while a planar surface of the waveguide defines a floor or ceiling of said reservoir, the planar surface being associated in part with capture molecules;

an inlet and outlet in fluid communication with said reservoir for infusing and draining said biological liquid into said reservoir so as to allow the biological liquid to contact said capture molecules;

a light detector for detecting light passed through said planar surface, which generates a signal indicating the intensity of said detected light; and a controller for monitoring the intensity signal and correlates said signal to the concentration of said analyte of interest in said biological sample.

7. The method according to claim 1, wherein said at least one analyte of interest is a marker released from cardiac tissue only after a myocardial infarction.

8. The method according to claim 7, wherein said marker is selected from the group consisting of myoglobin and serum glutamic oxalacetic transaminase.

9. The method according to claim 1, wherein said at least one analyte of interest is a cardiac specific marker.

10. The method according to claim 9, wherein said cardiac specific marker comprises at least one of troponin I, troponin T, and CK-MB.

11. The method according to claim 1, wherein said determining the concentration comprises simultaneously determining the concentrations of a plurality of analytes of interest in said biological liquid sample.

12. The method according to claim 1, further comprising continuing with said determining until a reliable determination is made of whether said at least one analyte is present in an amount indicative of a metabolic or disease state.

13. The method according to claim 12, further comprising reporting said reliable determination.

14. The method according to claim 13, wherein said reporting is effected by an audio or visual alarm.

15. A method of diagnosing a cardiac disease state in a patient, the method comprising:

providing an assay system which:

receives a biological liquid sample from the patient, the sample potentially containing at least one analyte selected from the group consisting of troponin-I, CK-MB, myoglobin, and mixtures thereof; and outputs a light signal indicative of a reaction between said at least one analyte and a reactive element within the assay system;

continuously measuring light emitted from said assay system over time;

continuously correlating the reaction to a concentration of said at least one analyte; and determining the concentration of said at least one analyte in said biological liquid sample based on said correlation of said emitted light in a time period less than about five minutes.

16. The method according to claim 15, wherein the determination of the concentration comprises simultaneously determining the concentrations of a plurality of analytes of interest potentially in the sample.

17. The method according to claim 15, further comprising:

continuing with said determination until a reliable determination is made of whether said at least one analyte is present in an amount indicative of a metabolic or disease state.

18. The method according to claim 17, further comprising reporting said reliable determination.

19. The method according to claim 18, wherein the report of the reliability determination is effected by an audio or visual alarm.

* * * * *